(12) United States Patent
Kim et al.

(10) Patent No.: US 11,370,779 B2
(45) Date of Patent: Jun. 28, 2022

(54) PHARMACEUTICAL COMPOSITION FOR PREVENTING OR TREATING ACUTE MYELOID LEUKEMIA OR METASTATIC BREAST CANCER

(71) Applicant: PELEMED CO., LTD., Seoul (KR)

(72) Inventors: Yong Chui Kim, Gwangju (KR); Pyeong-Hwa Jeong, Gwangju (KR)

(73) Assignee: PELEMED CO., LTD., Seoul (KR)

( * ) Notice: Subject to any disclaimer, the term of this patent is extended or adjusted under 35 U.S.C. 154(b) by 75 days.

(21) Appl. No.: 16/862,923

(22) Filed: Apr. 30, 2020

(65) Prior Publication Data

US 2020/0270229 A1 Aug. 27, 2020

Related U.S. Application Data

(63) Continuation-in-part of application No. PCT/KR2018/013051, filed on Oct. 30, 2018.

(30) Foreign Application Priority Data

Oct. 31, 2017 (KR) .................. 10-2017-0144142

(51) Int. Cl.
| | |
|---|---|
| C07D 403/04 | (2006.01) |
| A61P 35/00 | (2006.01) |
| C07D 401/14 | (2006.01) |
| C07D 403/14 | (2006.01) |
| C07D 413/14 | (2006.01) |

(52) U.S. Cl.
CPC ............ C07D 403/04 (2013.01); A61P 35/00 (2018.01); C07D 401/14 (2013.01); C07D 403/14 (2013.01); C07D 413/14 (2013.01)

(58) Field of Classification Search
CPC .. C07D 403/04; C07D 403/14; C07D 413/14; C07D 401/14; A61P 35/00
See application file for complete search history.

(56) References Cited

U.S. PATENT DOCUMENTS

| | | | | |
|---|---|---|---|---|
| 8,552,053 | B2 * | 10/2013 | Meijer ............... | A61P 35/02 514/418 |
| 2014/0275168 | A1 | 9/2014 | Nam et al. | |
| 2015/0259288 | A1 | 9/2015 | Nam et al. | |
| 2016/0243077 | A1 * | 8/2016 | Brown ............... | C07K 16/40 |

FOREIGN PATENT DOCUMENTS

| | | |
|---|---|---|
| EP | 2518139 A1 | 10/2012 |
| KR | 10-2005-0077173 A | 8/2005 |
| KR | 10-2016-0006669 A | 1/2016 |
| WO | 00/61555 A1 | 10/2000 |
| WO | 2005/070416 A1 | 8/2005 |
| WO | 2011/096676 A2 | 8/2011 |

OTHER PUBLICATIONS

Han et al., "Effects of indirubin derivatives on the FLT3 activity and growth of acute myeloid leukemia cell lines," Drug Development Research, 71: 221-227 (2010).
Marko et al., "Inhibition of cyclin-dependent kinase 1 (CDK1) by indirubin derivatives in human tumour cells," British Journal of Cancer, 84 (2): 283-289 (2001).
Stirewalt et al., "The role of FLT3 in haematopoietic malignancies," Nature, 3: 650-665 (2003).
Yamamoto et al., "Activating mutation of D835 within the activation loop of FLT3 in human hematologic malignancies," Blood, 97: 2434-2439 (2001).
Thiede et al., "Analysis of FLT3-activating mutations in 979 patients with acute myelogenous leukemia: association with FAB subtypes and identification of subgroups with poor prognosis," Blood, 99 (12): 4326-4335 (2002).
Schnittger et al., "Analysis of FLT3 length mutations in 1003 patients with acute myeloid leukemia: correlation to cytogenetics, FAB subtype, and prognosis in the AMLCG study and usefulness as a marker for the detection of minimal residual disease," Presented in part at the 42nd annual meeting of American Society of Hematology, Blood, 100 (1): 59-66 (2002).
Smith et al., "Validation of ITD mutations in FLT3 as a therapeutic target in human acute myeloid leukaemia," Nature (2012).
Welch et al., "The origin and evolution of mutations in acute myeloid leukemia," Cell, 150: 264-278 (2012).
Smith et al., "Single-agent CEP-701, a novel FLT3 inhibitor, shows biologic and clinical activity in patients with relapsed or refractory acute myeloid leukemia," Blood, 103 (10): 3669-3676 (2004).
Stone et al., "Patients with acute myeloid leukemia and an activating mutation in FLT3 respond to a small-molecule FLT3 tyrosine kinase inhibitor, PKC412," Blood, 105 (1): 54-60 (2005).
DeAngelo et al., "Phase 1 clinical results with tandutinib (MLN518), a novel FLT3 antagonist, in patients with acute myelogenous leukemia or high-risk myelodysplastic syndrome: safety, pharmacokinetics, and pharmacodynamics," 108: 3674-3681 (2006).
Zhang et al., "Mutant FLT3: A Direct Target of Sorafenib in Acute Myelogenous Leukemia," JNCI, 100 (3): 184-198 (2008).
Shiotsu et al., "KW-2449, a novel multikinase inhibitor, suppresses the growth of leukemia cells with FLT3 mutations or T315l-mutated BCR/ABL translocation," Blood, 114 (8): 1607-1617 (2006).
Zarrinkar et al., "AC220 is a uniquely potent and selective inhibitor of FLT3 for the treatment of acute myeloid leukemia (AML)," Blood, 114 (14): 2984-2992 (2009).
Knapper et al., "A phase 2 trial of the FLT3 inhibitor lestaurtinib (CEP701) as first-line treatment for older patients with acute myeloid leukemia not considered fit for intensive chemotherapy," Blood, 108 (10): 3262-3270 (2006).

(Continued)

Primary Examiner — Paul V Ward
(74) Attorney, Agent, or Firm — Morgan, Lewis & Bockius LLP

(57) ABSTRACT

The present invention relates to a pharmaceutical composition for preventing or treating acute myeloid leukemia or metastatic breast cancer, comprising, as an active ingredient, an indirubin derivative. When the compound of the present invention is used, it can effectively inhibit the activity of FLT3 kinase and can be usefully used to prevent or treat acute myeloid leukemia or metastatic breast cancer.

20 Claims, 4 Drawing Sheets

(56) References Cited

OTHER PUBLICATIONS

De Angelo et al., "Phase II Evaluation of the Tyrosine Kinase Inhibitor MLN518 in Patients with Acute Myeloid Leukemia (AML) Bearing a FLT3 Internal Tandem Duplication (ITD) Mutation," Blood, Poster Sessions, 104 (11): 1792 (2004).
Ravandi et al., "Phase I/II study of combination therapy with sorafenib, idarubicin, and cytarabine in younger patients with acute myeloid leukemia," Journal of Clinical Oncology, 28 (11): 1856-1862 (2010).
Pratz et al., "Incorporating FLT3 inhibitors into acute myeloid leukemia treatment regimens," Leukemia & Lymphoma, 49 (5): 852-863 (2008).
Small, "FLT3 mutations: biology and treatment," American Society of Hematology, 178-184 (2006).
Tasian et al., "Molecular therapeutic approaches for pediatric acute myeloid leukemia," Frontiers in Oncology, 4: Article 55 (2014).
Pratz et al., "Will FLT3 inhibitors fulfill their promise in acute meyloid leukemia," Current Opinion, 21 (2): (2014).
Pratz et al., "A pharmacodynamic study of the FLT3 inhibitor KW-2449 yields insight into the basis for clinical response," Blood, 113 (17): 3938-3946 (2009).
Abu-Duhier et al., "FLT3 internal tandem duplication mutations in adult acute myeloid leukaemia define a high-risk group," British Journal of Haematology, 111: 190-195 (2000).
Chou et al., "Theoretical Basis, Experimental Design, and Computerized Simulation of Synergism and Antagonism in Drug Combination Studies," Pharmacological Reviews, 58 (3): 621-681 (2006).
International Search Report issued in related International Patent Application No. PCT/KR2018/013051 dated Feb. 11, 2019.
Ichimaru et al., "5-Bromoindirubin 3'-(O-oxiran-2-ylmethyl)oxime: A long-acting anticancer agent and a suicide inhibitor for epoxide hydrolase," Bioorganic & Medicinal Chemistry, 25 (17): 4665-4676 (2017).
Kim et al., "5'-OH-5-nitro-Indirubin oxime (AGM130), an Indirubin derivative, induces apoptosis of Imatinib-resistant chronic myeloid leukemia cells," Leukemia Research, 37 (4): 427-433 (2013).
Nam et al., "Indirubin derivatives induce apoptosis of chronic myelogenous leukemia cells involving inhibition of Stat5 signaling," Molecular Oncology, 6 (3): 276-283 (2012).
Choi et al., "Indirubin derivatives as potent FLT3 inhibitors with anti-proliferative activity of acute myeloid leukemic cells," Bioorganic & Medicinal Chemistry Letters, 20 (6): 2033-2037 (2010).
Ginzinger et al., "Water-Soluble Cationic Derivatives of Indirubin, the Active Anticancer Component from Indigo naturalis," Chemistry & Biodiversity, 9 (10): 2175-2185 (2012).
CAS Registry No. 1591767-01-9; STN Entry date Apr. 28, 2014.
Cheng et al., "Identification of a Water-Soluble Indirubin Derivative as Potent Inhibitor of Insulin-like Growth Factor 1 Receptor through Structural Modification of the Parent Natural Molecule," Journal of Medicinal Chemistry, 60 (12): 1949-4962 (2017).
Choi et al., "5,5'-Substituted Indirubin-3'-oxime Derivatives as Potent Cyclin-Dependent Kinase Inhibitors with Anticancer Activity," Journal of Medicinal Chemistry, 53 (9): 3696-3706 (2010).

* cited by examiner

[FIG. 1]
A
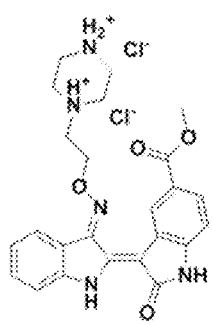
LDD-1937
B
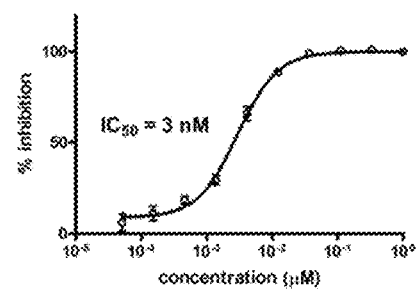
[FIG. 2]
A
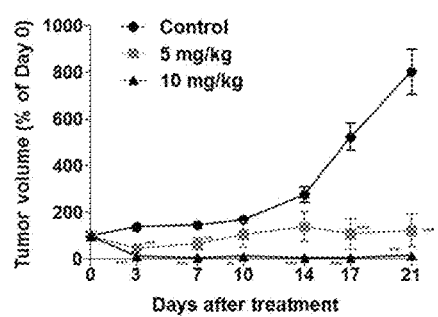
B
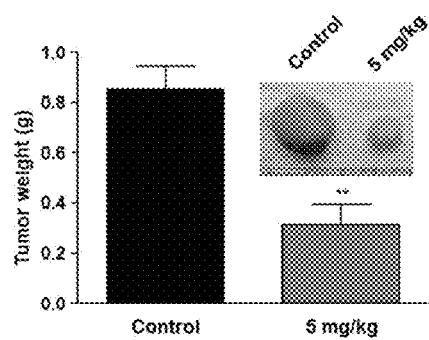

[FIG. 3]
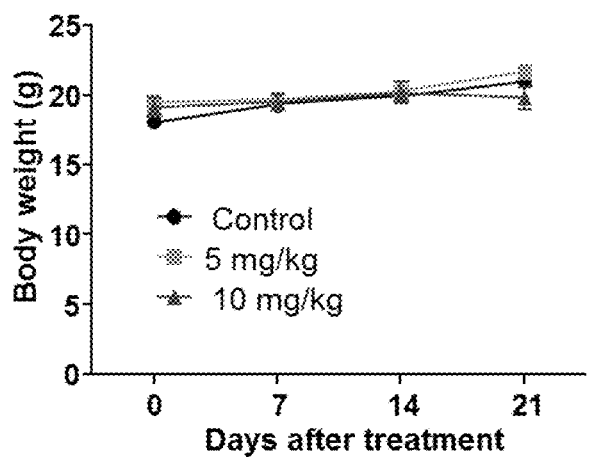
[FIG. 4]
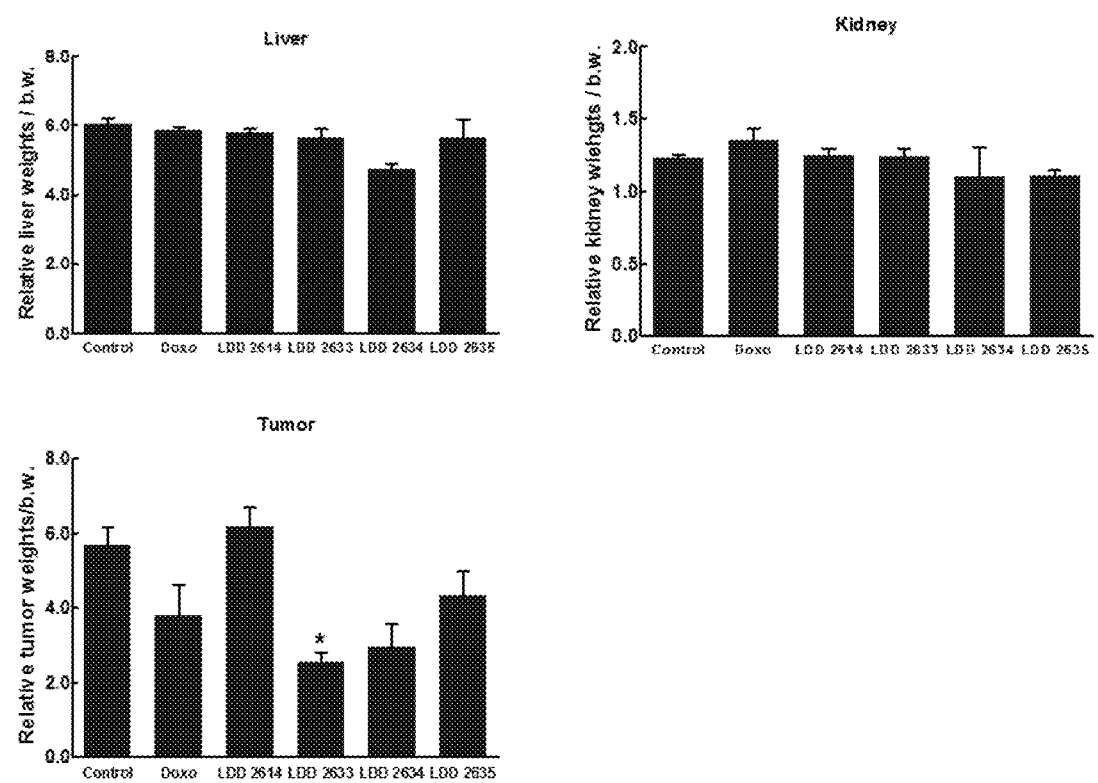

[FIG. 5]
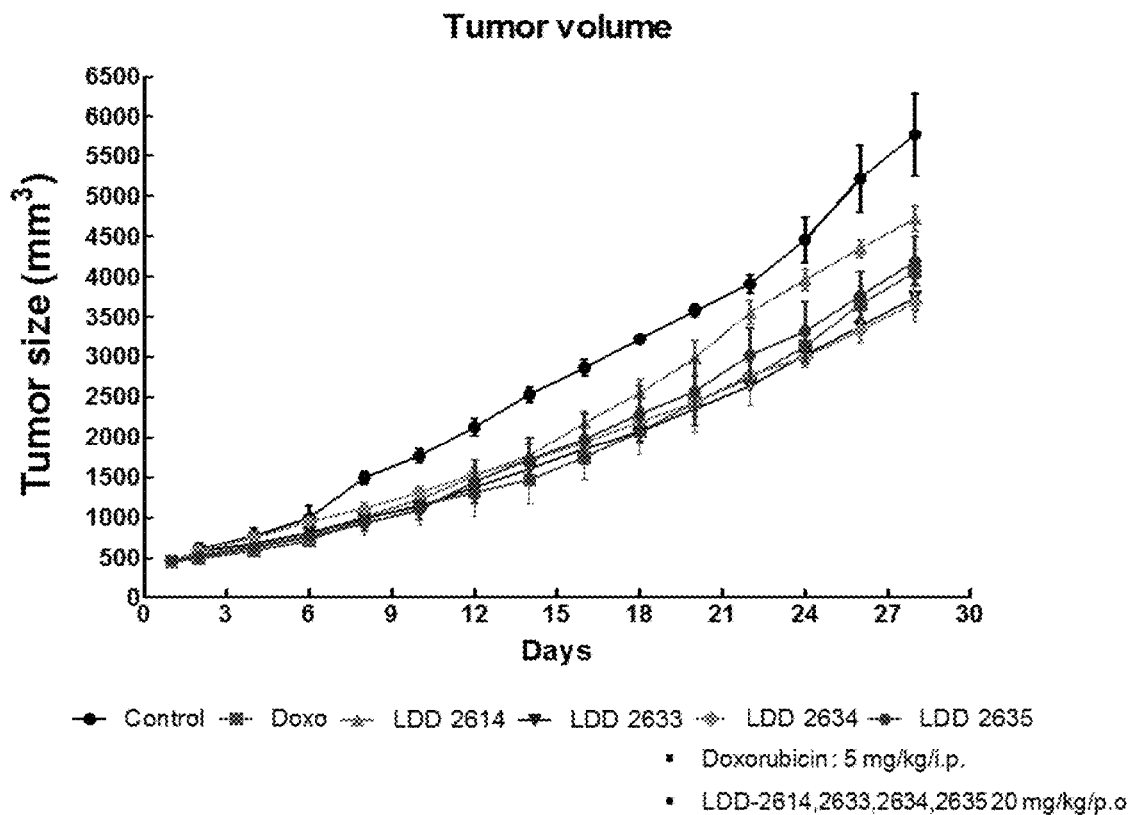
[FIG. 6]
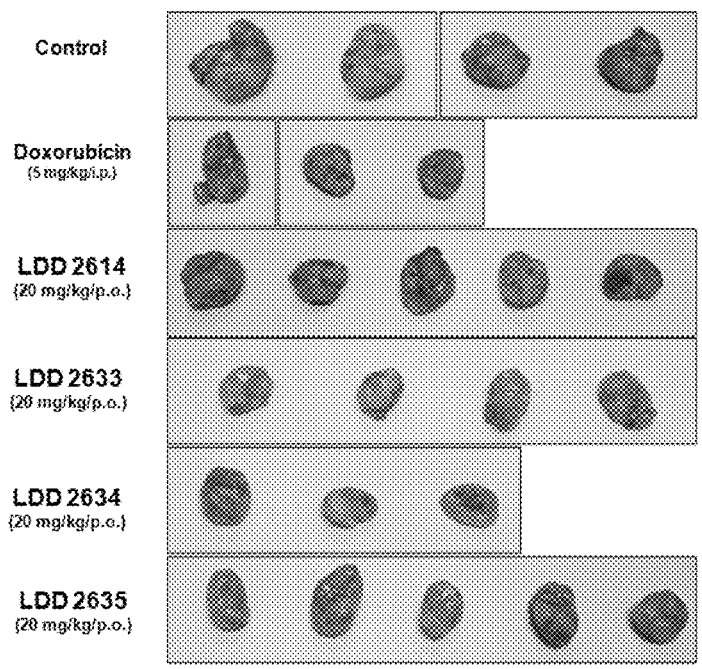

[FIG. 7]
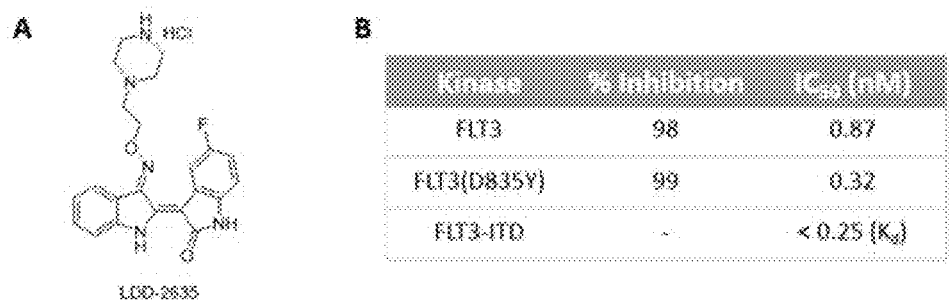
[FIG. 8]
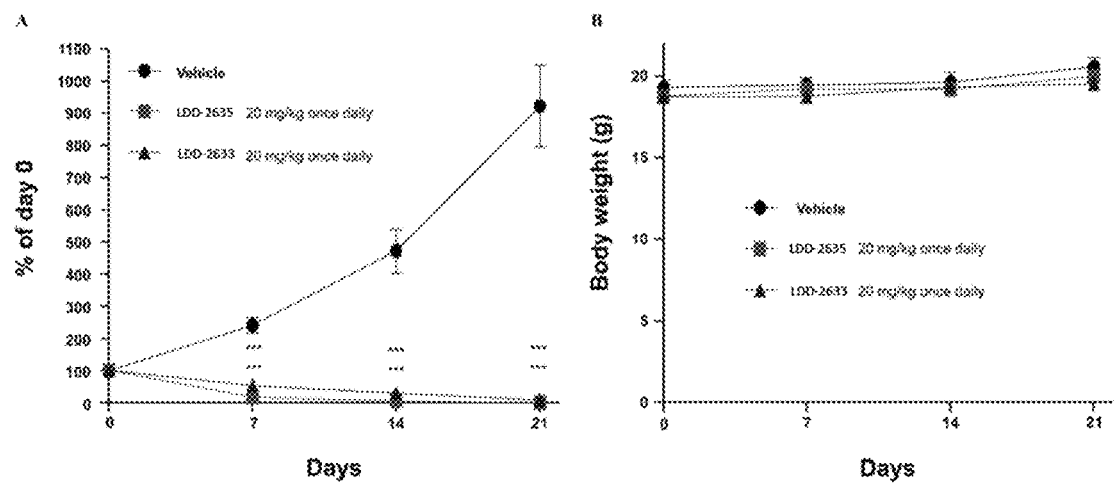

PHARMACEUTICAL COMPOSITION FOR PREVENTING OR TREATING ACUTE MYELOID LEUKEMIA OR METASTATIC BREAST CANCER

TECHNICAL FIELD

The present invention relates to a pharmaceutical composition for preventing or treating acute myeloid leukemia or metastatic breast cancer, comprising, as an active ingredient, an indirubin derivative.

BACKGROUND ART

FMS-like tyrosine kinase-3 (FLT-3), a receptor tyrosine kinase (RTK) belonging to the type III RTK family, plays an important role in the survival and proliferation of hematopoietic cells [1]. Activation of FLT3 is initiated by the binding of the FLT3 ligand, which is expressed by stromal cells, to the receptor. As a result, the FLT3 receptor dimerization and autophosphorylation trigger the downstream signaling pathways, which are categorized into PI3K/AKT, RAS/MAPK and STATS signaling pathways [2]. The FLT3 receptor is expressed at high levels in 70 to 100% of AML cells. The significance of FLT3 in leukemia has been thoroughly investigated, and the population of the FLT3 mutations has been reported to be approximately ⅓ of all AML patients [3]. Two major types of FLT3 mutations have been identified so far: internal tandem duplication (ITD) mutations in the juxtamembrane region and point mutations in the kinase domain [4]. These mutations have an adverse prognostic influence in chemotherapy failure and relapse [5-8]. Additionally, recent studies have shown that FLT3-ITD mutations represent a driver mutation for the progression of AML and valid therapeutic targets in AML [9-10]. Therefore, many researchers and pharmaceutical companies have attempted to find FLT3 inhibitors as potential therapeutic agents for AML.

Several clinical candidates targeting FLT3 have been reported including lestaurtinib [11], midostaurin [12], tandutinib [13], sorafenib [14], KW-2449 [15], and quizartinib [16]. Among them, lestaurtinib and midostaurin are indolocarbazole derivatives and well known multi-targeted tyrosine kinase inhibitors. Tandutinib, a piperazinyl-quinazoline compound, inhibits FLT3 as well as c-Kit and PDGFR. Most of these inhibitors were redirected to AML by the inhibition of the FLT3-ITD mutation from their initial purpose of targeting other kinases. Further, palbociclib, which was used as a therapeutic agent for breast cancer as an FLT3 inhibitor, has been found to be effective in treating AML patients, and thus, it can be judged that FLT3 inhibitors can be used for both breast cancer and acute myeloid leukemia.

It seems that most of the current FLT3 inhibitors are unimpressive mainly because of their low efficacy and target selectivity, except for quizartinib [17-20]. Therefore, the development of potent FLT3 kinase inhibitors is strongly needed at the present time.

A number of papers and patent documents have been cited throughout the present specification, and their citations have been indicated. The content of the cited papers and patent documents is incorporated herein by reference in their entirety, and the level of technical field to which the present invention belongs and the contents of the present invention will be described more clearly.

PRIOR ART DOCUMENTS

Non-Patent Documents

[1] S. D. Lyman, L. James, J. Zappone, P. R. Sleath, M. P. Beckmann, T. Bird, Characterization of the protein encoded by the flt3 (flk2) receptor-like tyrosine kinase gene, Oncogene. 8 (1993) 815-822. https://www.scopus.com/inward/record.uri?eid=2-s2.0-0027409749&partnerID=40&md5=ca39f6e31e1f6fea56547e6d4398e-79d.

[2] D. L. Stirewalt, J. P. Radich, The role of FLT3 in haematopoietic malignancies, Nat. Rev. Cancer. 3 (2003) 650-665. https://www.scopus.com/inward/record.uri?eid=2-s2.0-0141465061&partnerID=40&md5=74c5-831b6ffd9c07c920cdb2268e0abf.

[3] M. Nakao, S. Yokota, T. Iwai, H. Kaneko, S. Horiike, K. Kashima, Y. Sonoda, T. Fujimoto, S. Misawa, Internal tandem duplication of the flt3 gene found in acute myeloid leukemia, Leukemia. 10 (1996) 1911-1918. https://www.scopus.com/inward/record.uri?eid=2-s2.0-0030451722&partnerID=40&md5=55bd8efla7911069-8496bfafe5d74459.

[4] Y. Yamamoto, H. Kiyoi, Y. Nakano, R. Suzuki, Y. Kodera, S. Miyawaki, N. Asou, K. Kuriyama, F. Yagasaki, C. Shimazaki, H. Akiyama, K. Saito, M. Nishimura, T. Motoji, K. Shinagawa, A. Takeshita, H. Saito, R. Ueda, R. Ohno, T. Naoe, Activating mutation of D835 within the activation loop of FLT3 in human hematologic malignancies, Blood. 97 (2001) 2434-2439. doi:10.1182/blood.V97.8.2434.

[5] C. Thiede, C. Steudel, B. Mohr, M. Schaich, U. Schäkel, U. Platzbecker, M. Wermke, M. Bornhäuser, M. Ritter, A. Neubauer, G. Ehninger, T. Illmer, Analysis of FLT3-activating mutations in 979 patients with acute myelogenous leukemia: association with FAB subtypes and identification of subgroups with poor prognosis, Blood. 99 (2002).

[6] S. Schnittger, C. Schoch, M. Dugas, W. Kern, P. Staib, C. Wuchter, H. Löffler, C. M. Sauerland, H. Serve, T. Büchner, T. Haferlach, W. Hiddemann, Analysis of FLT3 length mutations in 1003 patients with acute myeloid leukemia: correlation to cytogenetics, FAB subtype, and prognosis in the AMLCG study and usefulness as a marker for the detection of minimal residual disease, Blood. 100 (2002).

[7] F. M. Abu-Duhier, A. C. Goodeve, G. A. Wilson, M. A. Gari, I. R. Peake, D. C. Rees, E. A. Vandenberghe, P. R. Winship, J. T. Reilly, FLT3 internal tandem duplication mutations in adult acute myeloid leukaemia define a high-risk group, Br. J. Haematol. 111 (2000) 190-195. doi:10.1046/j.1365-2141.2000.02317.x.

[8] L.-Y. Shih, C.-F. Huang, J.-H. Wu, T.-L. Lin, P. Dunn, P.-N. Wang, M.-C. Kuo, C.-L. Lai, H.-C. Hsu, Internal tandem duplication of FLT3 in relapsed acute myeloid leukemia: a comparative analysis of bone marrow samples from 108 adult patients at diagnosis and relapse, Blood. 100 (2002).

[9] C. C. Smith, Q. Wang, C.-S. Chin, S. Salerno, L. E. Damon, M. J. Levis, A. E. Perl, K. J. Travers, S. Wang, J. P. Hunt, P. P. Zarrinkar, E. E. Schadt, A. Kasarskis, J. Kuriyan, N. P. Shah, Validation of ITD mutations in FLT3 as a therapeutic target in human acute myeloid leukaemia, Nature. 485 (2012) 260-263. doi:10.1038/nature11016.

[10] J. S. Welch, T. J. Ley, D. C. Link, C. A. Miller, D. E. Larson, D. C. Koboldt, L. D. Wartman, T. L. Lamprecht, F. Liu, J. Xia, C. Kandoth, R. S. Fulton, M. D. McLellan, D. J. Dooling, J. W. Wallis, K. Chen, C. C. Harris, H. K. Schmidt, J. M. Kalicki-Veizer, C. Lu, Q. Zhang, L. Lin, M. D. O'Laughlin, J. F. McMichael, K. D. Delehaunty, L. A. Fulton, V. J. Magrini, S. D. McGrath, R. T. Demeter, T. L. Vickery, J. Hundal, L. L. Cook, G. W. Swift, J. P. Reed, P. A. Alldredge, T. N. Wylie, J. R. Walker, M. A. Watson, S. E. Heath, W. D. Shannon, N. Varghese, R. Nagarajan, J. E. Payton, J. D. Baty, S. Kulkarni, J. M. Klco, M. H. Tomasson, P. Westervelt, M. J. Walter, T. A. Graubert, J. F. DiPersio, L. Ding, E. R. Mardis, R. K. Wilson, The Origin and Evolution of Mutations in Acute Myeloid Leukemia, Cell. 150 (2012) 264-278. doi: 10.1016/j.cell.2012.06.023.
[11] B. D. Smith, M. Levis, M. Beran, F. Giles, H. Kantarjian, K. Berg, K. M. Murphy, T. Dauses, J. Allebach, D. Small, Single-agent CEP-701, a novel FLT3 inhibitor, shows biologic and clinical activity in patients with relapsed or refractory acute myeloid leukemia, Blood. 103 (2004).
[12] R. M. Stone, D. J. DeAngelo, V. Klimek, I. Galinsky, E. Estey, S. D. Nimer, W. Grandin, D. Lebwohl, Y. Wang, P. Cohen, E. A. Fox, D. Neuberg, J. Clark, D. G. Gilliland, J. D. Griffin, Patients with acute myeloid leukemia and an activating mutation in FLT3 respond to a small-molecule FLT3 tyrosine kinase inhibitor, PKC412, Blood. 105 (2004).
[13] D. J. DeAngelo, R. M. Stone, M. L. Heaney, S. D. Nimer, R. L. Paquette, R. B. Klisovic, M. A. Caligiuri, M. R. Cooper, J.-M. Lecerf, M. D. Karol, S. Sheng, N. Holford, P. T. Curtin, B. J. Druker, M. C. Heinrich, Phase 1 clinical results with tandutinib (MLN518), a novel FLT3 antagonist, in patients with acute myelogenous leukemia or high-risk myelodysplastic syndrome: safety, pharmacokinetics, and pharmacodynamics, Blood. 108 (2006).
[14] W. Zhang, M. Konopleva, Y. Shi, T. McQueen, D. Harris, X. Ling, Z. Estrov, A. Quintas-Cardama, D. Small, J. Cortes, M. Andreeff, Mutant FLT3: a direct target of sorafenib in acute myelogenous leukemia, J. Natl. Cancer Inst. 100 (2008) 184-98. doi:10.1093/jnci/djm328.
[15] Y. Shiotsu, H. Kiyoi, Y. Ishikawa, R. Tanizaki, M. Shimizu, H. Umehara, K. Ishii, Y. Mori, K. Ozeki, Y. Minaini, A. Abe, H. Maeda, T. Akiyama, Y. Kanda, Y. Sato, S. Akinaga, T. Naoe, KW-2449, a novel multikinase inhibitor, suppresses the growth of leukemia cells with FLT3 mutations or T315I-mutated BCR/ABL translocation, Blood. 114 (2009).
[16] P. P. Zarrinkar, R. N. Gunawardane, M. D. Cramer, M. F. Gardner, D. Brigham, B. Belli, M. W. Karaman, K. W. Pratz, G. Pallares, Q. Chao, K. G. Sprankle, H. K. Patel, M. Levis, R. C. Armstrong, J. James, S. S. Bhagwat, AC220 is a uniquely potent and selective inhibitor of FLT3 for the treatment of acute myeloid leukemia (AML), Blood. 114 (2009).
[17] S. Knapper, A. K. Burnett, T. Littlewood, W. J. Kell, S. Agrawal, R. Chopra, R. Clark, M. J. Levis, D. Small, A phase 2 trial of the FLT3 inhibitor lestaurtinib (CEP701) as first-line treatment for older patients with acute myeloid leukemia not considered fit for intensive chemotherapy, Blood. 108 (2006).
[18] D. J. De Angelo, R. M. Stone, M. L. Heaney, S. D. Nimer, R. Paquette, R. Bruner-Klisovic, M. A. Caligiuri, M. R. Cooper, J.-M. LeCerf, G. Iyer, M. C. Heinrich, B. J. Druker, Phase II Evaluation of the Tyrosine Kinase Inhibitor MLN518 in Patients with Acute Myeloid Leukemia (AML) Bearing a FLT3 Internal Tandem Duplication (ITD) Mutation, Blood. 104 (2015).
[19] F. Ravandi, J. E. Cortes, D. Jones, S. Faderl, G. Garcia-Manero, M. Y. Konopleva, S. O'Brien, Z. Estrov, G. Borthakur, D. Thomas, S. R. Pierce, M. Brandt, A. Byrd, B. N. Bekele, K. Pratz, R. Luthra, M. Levis, M. Andreeff, H. M. Kantarjian, Phase study of combination therapy with sorafenib, idarubicin, and cytarabine in younger patients with acute myeloid leukemia, J. Clin. Oncol. 28 (2010) 1856-62. doi:10.1200/JC0.2009.25.4888.
[20] K. W. Pratz, J. Cortes, G. J. Roboz, N. Rao, O. Arowojolu, A. Stine, Y. Shiotsu, A. Shudo, S. Akinaga, D. Small, J. E. Karp, M. Levis, A pharmacodynamic study of the FLT3 inhibitor KW-2449 yields insight into the basis for clinical response, Blood. 113 (2009).
[21] S. J. Choi, M. J. Moon, S. D. Lee, S.-U. Choi, S.-Y. Han, Y.-C. Kim, Indirubin derivatives as potent FLT3 inhibitors with anti-proliferative activity of acute myeloid leukemic cells, 2010. doi:10.10164bmc1.2010.01.039.
[22] T.-C. Chou, Theoretical Basis, Experimental Design, and Computerized Simulation of Synergism and Antagonism in Drug Combination Studies, Pharmacol. Rev. 58 (2006).
[23] K. Pratz, M. Levis, Incorporating FLT3 inhibitors into acute myeloid leukemia treatment regimens, Leuk. Lymphoma. 49 (2008) 852-863. doi:10.1080/10428190801895352.
[24] J. T. DiPiro, R. L. Talbert, G. C. Yee, B. G. Wells, L. M. Posey, Pharmacotherapy A Pathophysiologic Approach 9/E, McGraw-Hill Education2014.
[25] D. Small, FLT3 mutations: biology and treatment, Hematol. Am. Soc. Hematol. Educ. Progr. 2006 (2006) 178-84. doi:10.1182/asheducation-2006.1.178.
[26] S. K. Tasian, J. A. Pollard, R. Aplenc, Molecular Therapeutic Approaches for Pediatric Acute Myeloid Leukemia, Front. Oncol. 4 (2014) 55. doi:10.3389/fonc.2014.00055.
[27] K. W. Pratz, S. M. Luger, Will FLT3 inhibitors fulfill their promise in acute meyloid leukemia, Curr. Opin. Hematol. 21 (2014) 72-78. doi:10.1097/MOH.0000000000000022.

DISCLOSURE

Technical Problem

The present inventors have made extensive efforts to find out novel compounds having a FLT3 kinase inhibitory ability. As a result, they have identified that predetermined indirubin derivative compounds can effectively inhibit the FLT3 kinase, thereby completing the present invention.

Accordingly, an object of the present invention is to provide a novel compound having a FLT3 inhibitory ability, a pharmaceutically acceptable salt, a solvate or a hydrate thereof.

Another object of the present invention is to provide a pharmaceutical composition for preventing or treating acute myeloid leukemia.

Still another object of the present invention is to provide a pharmaceutical composition for preventing or treating metastatic breast cancer.

Other objects and advantages of the present invention will become apparent from the detailed description together with the appended claims and drawings.

Technical Solution

According to an aspect of the present invention, the present invention provides a compound represented by Chemical Formula 1 below, a pharmaceutically acceptable salt, a solvate or a hydrate thereof:

[Chemical Formula 1]

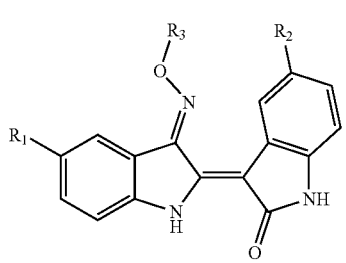

in the Chemical Formula 1, $R_1$ is hydrogen, fluoro, or hydroxy, $R_2$ is hydrogen, halogen, nitro, carboxyl, $C_1$-$C_4$ alkyl ester, or $C_1$-$C_4$ alkoxy substituted or unsubstituted with halogen, and $R_3$ is hydrogen, 2-bromoethyl,

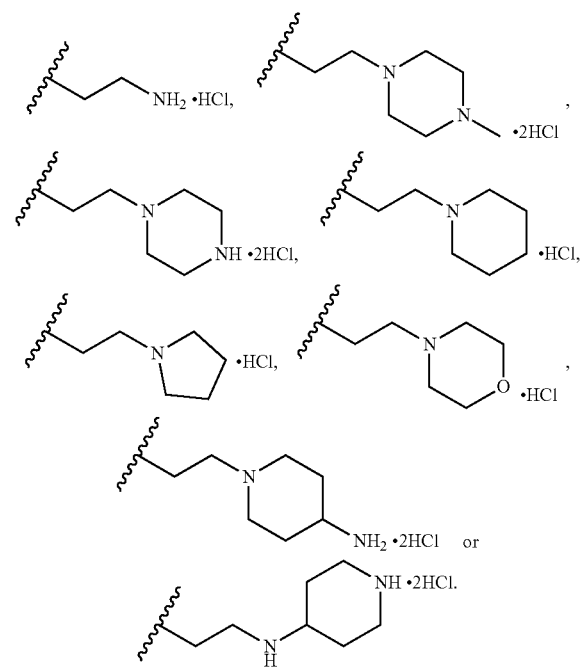

The present inventors have made extensive efforts to develop novel FLT3 kinase inhibitors, and as a result, they have identified that predetermined indirubin derivative compounds can effectively inhibit the FLT3 kinase.

In one specific embodiment of the present invention, the $R_3$ of the present invention is any one of substituents selected from the group consisting of 2-bromoethyl,

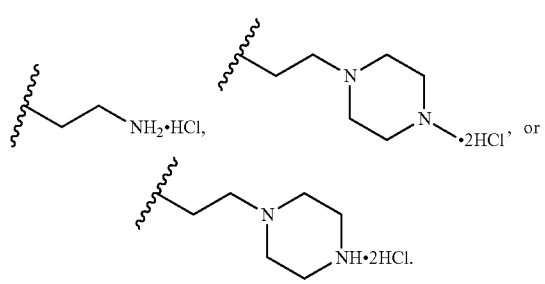

More preferably, the $R_3$ of the present invention is any one of substituents selected from the group consisting of

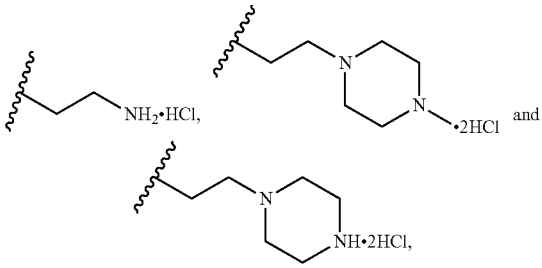

even more preferably,

In one specific embodiment of the present invention, the $R_2$ of the present invention is $C_1$-$C_4$ alkyl ester. The $C_1$-$C_4$ alkyl substituent included in the $C_1$-$C_4$ alkyl ester of one specific embodiment of the present invention includes both straight or branched $C_1$-$C_4$ alkyl groups, and specifically, it may be, for example, methyl, ethyl, n-propyl, iso-propyl, n-butyl, sec-butyl, iso-butyl, or tert-butyl. When the $R_1$ of the present invention is an alkyl ester substituent of a compound rather than a carboxyl substituent of a compound, it has a smaller $IC_{50}$ value for FLT3 kinase, and thus may be more effective in inhibiting FLT3 kinase.

In one specific embodiment of the present invention, the $R_2$ of the present invention is halogen. Specifically, the halogen may be fluorine, chlorine, bromine, or iodine.

In one specific embodiment of the present invention, the $R_2$ of the present invention is $C_1$-$C_4$ alkoxy substituted or unsubstituted with halogen. The $C_1$-$C_4$ alkyl substituent included in the $C_1$-$C_4$ alkoxy of one specific embodiment of the present invention includes both straight or branched $C_1$-$C_4$ alkyl groups, specifically, it may be, for example, methyl, ethyl, n-propyl, iso-propyl, n-butyl, sec-butyl, iso-butyl, or tert-butyl. Specifically, the $C_1$-$C_4$ alkoxy substituted with halogen may be $C_1$-$C_4$ alkoxy fluoride, and more specifically, trifluoromethoxy.

In one specific embodiment of the present invention, the $C_1$-$C_4$ alkyl ester of the present invention is methyl ester.

In one specific embodiment of the present invention, the $R_2$ of the present invention is $C_1$-$C_4$ alkyl ester, and $R_3$ is any one of substituents selected from the group consisting of

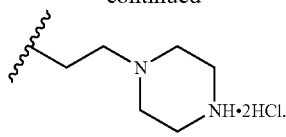

In one specific embodiment of the present invention, the compound represented by the Chemical Formula of the present invention may be any one selected from the group consisting of the following compounds: methyl (2Z,3E)-2'-oxo-3-((2-(piperazin-1-yl)ethoxy)imino)-[2,3'-biindolinylidene]-5'-carboxylate dihydrochloride (Compound 4), methyl (2Z,3E)-3-(hydroxyimino)-2'-oxo-[2,3'-biindolinylidene]-5'-carboxylate (Compound 1), methyl (2Z,3E)-3-((2-bromoethoxy)imino)-2'-oxo-[2,3'-biindolinylidene]-5'-carboxylate (Compound 2), methyl (2Z,3E)-3-((2-aminoethoxy)imino)-2'-oxo-[2,3'-biindolinylidene]-5'-carboxylate hydrochloride (Compound 3), methyl (2Z,3E)-3-((2-(4-methylpiperazin-1-yl)ethoxy)imino)-2'-oxo-[2,3'-biindolinylidene]-5'-carboxylate dihydrochloride (Compound 5), methyl (2Z,3E)-3-((2-morpholinoethoxy)imino)-2'-oxo-[2,3'-biindolinylidene]-5'-carboxylate hydrochloride (Compound 6), (2Z,3E)-3-((2-bromoethoxy)imino)-2'-oxo-[2,3'-biindolinylidene]-5'-carboxylic acid (Compound 8), (2Z,3E)-3-((2-aminoethoxy)imino)-2'-oxo-[2,3'-biindolinylidene]-5'-carboxylic acid hydrochloride (Compound 9), (2Z,3E)-2'-oxo-3-((2-(piperazin-1-yl)ethoxy)imino)-[2,3'-biindolinylidene]-5'-carboxylic acid dihydrochloride (Compound 10), (2Z,3E)-3-(4-methylpiperazin-1-yl)ethoxy)imino)-2'-oxo-[2,3'-biindolinylidene]-5'-carboxylic acid dihydrochloride (Compound 11), (2Z,3E)-3-((2-morpholinoethoxy)imino)-2'-oxo-[2,3'-biindolinylidene]-5'-carboxylate hydrochloride (Compound 12), (2Z,3E)-5-hydroxy-3-((2-(4-methylpiperazin-1-yl)ethoxy)imino)-5'-nitro-[2,3'-biindolinylidene]-2'-one dihydrochloride (Compound 14), (2Z,3E)-3-((2-amino ethoxy)imino)-5'-nitro-[2,3'-biindolinylidene]-2'-one hydrochloride (Compound 15), (2Z 3E)-5'-nitro-34(2-(piperazin-1-yl)ethoxy)imino)-[2,3'-biindolinylidene]-2'-one dihydrochloride (Compound 16), (2Z,3E)-5-fluoro-5'-nitro-3-((2-(piperazin-1-yl)ethoxy)imino)-[2,3'-biindolinylidene]-2'-one dihydrochloride (Compound 17), (2Z,3E)-5-fluoro-3-((2-(4-methylpiperazin-1-yl)ethoxy)imino)-5'-nitro-[2,3'-biindolinylidene]-2'-one dihydrochloride (Compound 18), (2Z,3E)-5-fluoro-5'-nitro-3-((2-(piperidin-1-yl)ethoxy)imino)-[2,3'-biindolinylidene]-2'-one hydrochloride (Compound 19), (2Z,3E)-5-fluoro-5'-nitro-3-((2-(pyrrolidin-1-yl)ethoxy)imino)-[2,3'-biindolinylidene]-2'-one hydrochloride (Compound 20), (2Z,3E)-5,5'-difluoro-3-((2-(piperazin-1-yl)ethoxy)imino)-[2,3'-biindolinylidene]-2'-one dihydrochloride (Compound 21), (2Z,3E)-5,5'-difluoro-3-((2-(4-methylpiperazin-1-yl)ethoxy)imino)-[2,3'-biindolinylidene]-2'-one dihydrochloride (Compound 22), (2Z,3E)-5,5'-difluoro-3-((2-(piperidin-1-yl)ethoxy)imino)-[2,3'-biindolinylidene]-2'-one hydrochloride (Compound 23), (2Z,3E)-5,5'-difluoro-3-((2-(pyrrolidin-1-yl)ethoxy)imino)-[2,3'-biindolinylidene]-2'-one hydrochloride (Compound 24), (2Z,3E)-3-((2-(4-aminopiperidin-1-yl)ethoxy)imino)-5,5'-difluoro-[2,3'-biindolinylidene]-2'-one dihydrochloride (Compound 25), (2Z,3E)-5,5'-difluoro-3-((2-(piperidin-4-ylamino)ethoxy)imino)-[2,3'-biindolinylidene]-2'-one dihydrochloride (Compound 26), (2Z,3E)-5,5'-difluoro-3-((2-morpholinoethoxy)imino)-[2,3'-biindolinylidene]-2'-one hydrochloride (Compound 27), (2Z,3E)-5'-fluoro-3-((2-(piperazin-1-yl)ethoxy)imino)-[2,3'-biindolinylidene]-2'-one dihydrochloride (Compound 33), (2Z,3E)-5'-fluoro-3-((2-(4-methylpiperazin-1-yl)ethoxy)imino)-[2,3'-biindolinylidene]-2'-one dihydrochloride (Compound 34), (2Z,3E)-5'-fluoro-3-((2-(piperidin-1-yl)ethoxy)imino)-[2,3'-biindolinylidene]-2'-one hydrochloride (Compound 35), (2Z,3E)-5'-fluoro-3-((2-(pyrrolidin-1-yl)ethoxy)imino)-[2,3'-biindolinylidene]-2'-one hydrochloride (Compound 36), (2Z,3E)-5'-fluoro-3-((2-(piperidin-4-ylamino)ethoxy)imino)-[2,3'-biindolinylidene]-2'-one dihydrochloride (Compound 37), (2Z,3E)-5'-chloro-3-((2-(piperazin-1-yl)ethoxy)imino)-[2,3'-biindolinylidene]-2'-one dihydrochloride (Compound 38), (2Z,3E)-5'-chloro-3-((2-(4-methylpiperazin-1-yl)ethoxy)imino)-[2,3'-biindolinylidene]-2'-one dihydrochloride (Compound 39), (2Z,3E)-5'-bromo-3-((2-(piperazin-1-yl)ethoxy)imino)-[2,3'-biindolinylidene]-2'-one dihydrochloride (Compound 40), (2Z,3E)-5'-bromo-3-((2-(4-methylpiperazin-1-yl)ethoxy)imino)-[2,3'-biindolinylidene]-2'-one dihydrochloride (Compound 41), (2Z,3E)-5'-iodo-3-((2-(piperazin-1-yl)ethoxy)imino)-[2,3'-biindolinylidene]-2'-one dihydrochloride (Compound 42), (2Z,3E)-5'-iodo-3-((2-(4-methylpiperazin-1-yl)ethoxy)imino)-[2,3'-biindolinylidene]-2'-one dihydrochloride (Compound 43), (2Z,3E)-3-((2-(piperazin-1-yl)ethoxy)imino)-5'-(trifluoromethoxy)-[2,3'-biindolinylidene]-2'-one dihydrochloride (Compound 44), (2Z,3E)-3-((2-(4-methylpiperazin-1-yl)ethoxy)imino)-5'-(trifluoromethoxy)-[2,3'-biindolinylidene]-2'-one dihydrochloride (Compound 45), (2Z,3E)-5'-methoxy-3-((2-(piperazin-1-yl)ethoxy)imino)-[2,3'-biindolinylidene]-2'-one dihydrochloride (Compound 46), and (2Z,3E)-5'-methoxy-3-((2-(4-methylpiperazin-1-yl)ethoxy)imino)-[2,3'-biindolinylidene]-2'-one dihydrochloride (Compound 47).

In one specific embodiment of the present invention, the compound represented by the Chemical Formula 1 of the present invention may have an $IC_{50}$ value for FLT3 inhibition of 100 nM or less. More specifically, the compound represented by the Chemical Formula 1 may have an $IC_{50}$ value for FLT3 inhibition of 50 nM or less, even more specifically, 40 nM or less, even more specifically, 35 nM or less, even more specifically, 30 nM or less, even more specifically, 25 nM or less, even more specifically, 20 nM or less, even more specifically, 15 nM or less, and even more specifically, 10 nM or less.

According to another aspect of the present invention, the present invention provides a pharmaceutical composition for preventing or treating acute myeloid leukemia or metastatic breast cancer, including: (a) a compound represented by Chemical Formula 1 below, a pharmaceutically acceptable salt, a solvate, or a hydrate thereof; and (b) a pharmaceutically acceptable carrier:

[Chemical Formula 1]

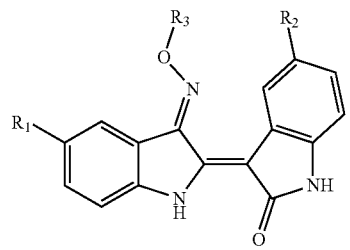

in the Chemical Formula 1, $R_1$ is hydrogen, fluoro, or hydroxy, $R_2$ is hydrogen, halogen, nitro, carboxyl, $C_1$-$C_4$ alkyl ester, or $C_1$-$C_4$ alkoxy substituted or unsubstituted with halogen, and $R_3$ is hydrogen, 2-bromoethyl,

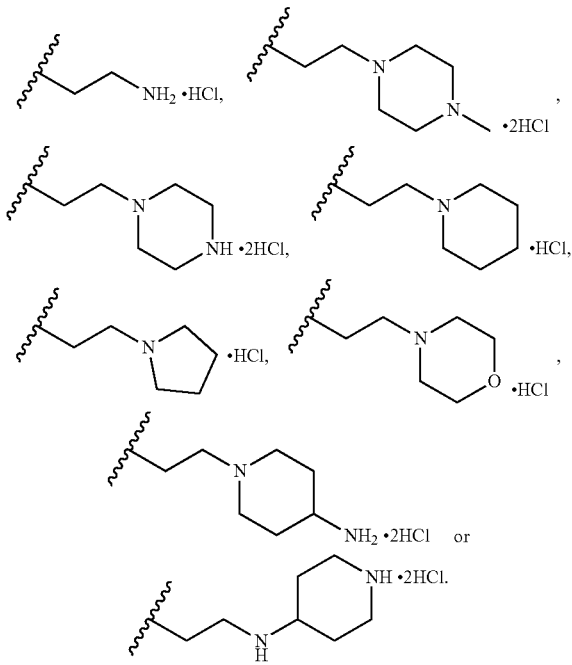

According to one embodiment of the present invention, the compound represented by the Chemical Formula 1 may be any one selected from the group consisting of the following compounds: methyl (2Z,3E)-2'-oxo-3-((2-(piperazin-1-yl)ethoxy)imino)-[2,3'-biindolinylidene]-5'-carboxylate dihydrochloride (Compound 4), methyl (2Z,3E)-3-(hydroxyimino)-2'-oxo-[2,3'-biindolinylidene]-5'-carboxylate (Compound 1), methyl (2Z,3E)-34(2-bromoethoxy)imino)-2'-oxo-[2,3'-biindolinylidene]-5'-carboxylate (Compound 2), methyl (2Z,3E)-3-((2-aminoethoxy)imino)-2'-oxo-[2,3'-biindolinylidene]-5'-carboxylate hydrochloride (Compound 3), methyl (2Z,3E)-3-(4-methylpiperazin-1-yl)ethoxy) imino)-2'-oxo-[2,3'-biindolinylidene]-5'-carboxylate dihydrochloride (Compound 5), methyl (2Z,3E)-3-((2-morpholinoethoxy)imino)-2'-oxo-[2,3'-biindolinylidene]-5'-carboxylate hydrochloride (Compound 6), (2Z,3E)-3-(hydroxyimino)-2'-oxo-[2,3'-biindolinylidene]-5'-carboxylic acid (Compound 7), (2Z,3E)-3-((2-bromoethoxy)imino)-2'-oxo-[2,3'-biindolinylidene]-5'-carboxylic acid (Compound 8), (2Z,3E)-3-((2-aminoethoxy)imino)-2'-oxo-[2,3'-biindolinylidene]-5'-carboxylic acid hydrochloride (Compound 9), (2Z,3E)-2'-oxo-3-((2-(piperazin-1-yl)ethoxy)imino)-[2,3'-biindolinylidene]-5'-carboxylic acid dihydrochloride (Compound 10), (2Z,3E)-3-((2-(4-methylpiperazin-1-yl)ethoxy)imino)-2'-oxo-[2,3'-biindolinylidene]-5'-carboxylic acid dihydrochloride (Compound 11), (2Z,3E)-3-((2-morpholinoethoxy)imino)-2'-oxo-[2,3'-biindolinylidene]-5'-carboxylate hydrochloride (Compound 12), (2Z,3E)-5-hydroxy-3-(hydroxyimino)-5'-nitro-[2,3'-biindolinylidene]-2'-one (Compound 13), (2Z,3E)-5-hydroxy-3-((2-(4-methylpiperazin-1-yl)ethoxy) imino)-5'-nitro-[2,3'-biindolinylidene]-2'-one dihydrochloride (Compound 14), (2Z,3E)-34(2-aminoethoxy)imino)-5'-nitro-[2,3'-biindolinylidene]-2'-one hydrochloride (Compound 15), (2Z,3E)-5'-nitro-3-((2-(piperazin-1-yl)ethoxy)imino)-[2,3'-biindolinylidene]-2'-one dihydrochloride (Compound 16), (2Z,3E)-5-fluoro-5'-nitro-3-((2-(piperazin-1-yl)ethoxy)imino)-[2,3'-biindolinylidene]-2'-one dihydrochloride (Compound 17), (2Z,3E)-5-fluoro-3-((2-(4-methylpiperazin-1-yl)ethoxy)imino)-5'-nitro-[2,3'-biindolinylidene]-2'-one dihydrochloride (Compound 18), (2Z,3E)-5-fluoro-5'-nitro-3-((2-(piperidin-1-yl)ethoxy)imino)-[2,3'-biindolinylidene]-2'-one hydrochloride (Compound 19), (2Z,3E)-5-fluoro-5'-nitro-3-((2-(pyrrolidin-1-yl)ethoxy)imino)-[2,3'-biindolinylidene]-2'-one hydrochloride (Compound 20), (2Z,3E)-5,5'-difluoro-3-((2-(piperazin-1-yl)ethoxy)imino)-[2,3'-biindolinylidene]-2'-one dihydrochloride (Compound 21), (2Z,3E)-5,5'-difluoro-3((2-(4-methylpiperazin-1-yl)ethoxy)imino)-[2,3'-biindolinylidene]-2'-one dihydrochloride (Compound 22), (2Z,3E)-5,5'-difluoro-3-((2-(piperidin-1-yl)ethoxy)imino)-[2,3'-biindolinylidene]-2'-one hydrochloride (Compound 23), (2Z,3E)-5,5'-difluoro-3-((2-(pyrrolidin-1-yl)ethoxy)imino)-[2,3'-biindolinylidene]-2'-one hydrochloride (Compound 24), (2Z,3E)-3-((2-(4-aminopiperidin-1-yl)ethoxy)imino)-5,5'-difluoro-[2,3'-biindolinylidene]-2'-one dihydrochloride (Compound 25), (2Z,3E)-5,5'-difluoro-3-((2-(piperidin-4-ylamino)ethoxy)imino)-[2,3'-biindolinylidene]-2'-one dihydrochloride (Compound 26), (2Z,3E)-5,5'-difluoro-3-((2-morpholinoethoxy)imino)-[2,3'-biindolinylidene]-2'-one hydrochloride (Compound 27), (2Z,3E)-3-((2-(piperazin-1-yl)ethoxy)imino)-[2,3'-biindolinylidene]-2'-one dihydrochloride (Compound 28), (2Z,3E)-3-((2-(4-methylpiperazin-1-yl)ethoxy)imino)-[2,3'-biindolinylidene]-2'-one dihydrochloride (Compound 29), (2Z,3E)-3-((2-(piperidin-1-yl)ethoxy)imino)-[2,3'-biindolinylidene]-2'-one hydrochloride (Compound 30), (2Z,3E)-3-((2-(pyrrolidin-1-yl)ethoxy)imino)-[2,3'-biindolinylidene]-2'-one hydrochloride (Compound 31), (2Z,3E)-3-((2-(piperidin-4-ylamino)ethoxy)imino)-[2,3'-biindolinylidene]-2'-one dihydrochloride (Compound 32), (2Z,3E)-5'-fluoro-3-((2-(piperazin-1-yl)ethoxy)imino)-[2,3'-biindolinylidene]-2'-one dihydrochloride (Compound 33), (2Z,3E)-5'-fluoro-3-((2-(4-methylpiperazin-1-yl)ethoxy)imino)-[2,3'-biindolinylidene]-2'-one dihydrochloride (Compound 34), (2Z,3E)-5'-fluoro-3-((2-(piperidin-1-yl)ethoxy)imino)-[2,3'-biindolinylidene]-2'-one hydrochloride (Compound 35), (2Z,3E)-5'-fluoro-3-((2-(pyrrolidin-1-yl)ethoxy)imino)-[2,3'-biindolinylidene]-2'-one hydrochloride (Compound 36), (2Z,3E)-5'-fluoro-3-((2-(piperidin-4-ylamino)ethoxy)imino)-[2,3'-biindolinylidene]-2'-one dihydrochloride (Compound 37), (2Z,3E)-5'-chloro-3-((2-(piperazin-1-yl)ethoxy)imino)-[2,3'-biindolinylidene]-2'-one dihydrochloride (Compound 38), (2Z,3E)-5'-chloro-3-((2-(4-methylpiperazin-1-yl)ethoxy)imino)-[2,3'-biindolinylidene]-2'-one dihydrochloride (Compound 39), (2Z,3E)-5'-bromo-3-((2-(piperazin-1-yl)ethoxy)imino)-[2,3'-biindolinylidene]-2'-one dihydrochloride (Compound 40), (2Z,3E)-5'-bromo-3-((2-(4-methylpiperazin-1-yl)ethoxy)imino)-[2,3'-biindolinylidene]-2'-one dihydrochloride (Compound 41), (2Z,3E)-5'-iodo-3-((2-(piperazin-1-yl)ethoxy)imino)-[2,3'-biindolinylidene]-2'-one dihydrochloride (Compound 42), (2Z,3E)-5'-iodo-3-((2-(4-methylpiperazin-1-yl)ethoxy)imino)-[2,3'-biindolinylidene]-2'-one dihydrochloride (Compound 43), (2Z,3E)-3-((2-(piperazin-1-yl)ethoxy)imino)-5-(trifluoromethoxy)-[2,3'-biindolinylidene]-2'-one dihydrochloride (Compound 44), (2Z,3E)-3-((2-(4-methylpiperazin-1-yl)ethoxy)imino)-5'-(trifluoromethoxy)-[2,3'-biindolinylidene]-2'-one dihydrochloride (Compound 45), (2Z,3E)-5'-methoxy-3-((2-(piperazin-1-yl)ethoxy)imino)-[2,3'-biindolinylidene]-2'-one dihydrochloride (Compound 46), and (2Z,3E)-5'-methoxy-3-((2-(4-methylpiperazin-1-yl)ethoxy)imino)-[2,3'-biindolinylidene]-2'-one dihydrochloride (Compound 47).

The pharmaceutical composition of the present invention includes a pharmaceutically acceptable carrier in addition to the active ingredients. The pharmaceutically acceptable carrier included in the pharmaceutical composition of the present invention is typically used in the formulation, and examples thereof include lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, and mineral oil, etc., but are not limited thereto. The pharmaceutical composition of the present invention may further include lubricants, wetting agents, sweeteners, aromatics, emulsifiers, suspensions, and preservatives, etc., in addition to the above components. Suitable pharmaceutically acceptable carriers and formulations are described in detail in Remington's Pharmaceutical Sciences (19th ed., 1995).

An appropriate dosage of the pharmaceutical composition of the present invention may be variously prescribed according to factors such as a formulation method, an administration method, a patient's age, weight, gender, and pathological condition, food, administration time, administration route, excretion speed, and reaction sensitivity. Meanwhile, the dosage of the pharmaceutical composition of the present invention may be preferably 1 to 1000 mg/kg (weight) per day.

The pharmaceutical composition of the present invention may be orally or parenterally administered, wherein in case of the parenteral administration, it may be locally applied to skin or administered through an intravenous injection, a subcutaneous injection, an intramuscular injection, an intraperitoneal injection, a transdermal administration, etc. Considering that the pharmaceutical composition of the present invention is applied for treating acute myeloid leukemia, the administration is preferably performed through an intravenous injection or oral administration.

The pharmaceutical composition of the present invention may be formulated using a pharmaceutically acceptable carrier and/or excipient according to a method which can be easily carried out by those skilled in the art to which the present invention pertains, and may be prepared in a unit dosage form or may be prepared by being packaged in a multi-dose container. In particular, the formulation may be in the form of a solution, a suspension or an emulsion in oil or water-soluble medium, or may be in the form of an extract, a powder, a granule, a tablet, or a capsule, and may further contain a dispersant or a stabilizer.

The pharmaceutical composition of the present invention may be administered orally. Examples of a solid preparation for oral administration include a tablet, a pill, a powder, a granule, a capsule, a troche, etc., and such solid preparations are formulated by mixing the compound of the present invention with at least one excipient, such as starch, calcium carbonate, sucrose or lactose, or gelatin, etc. In addition to simple excipients, lubricants such as magnesium stearate and talc are also used. Examples of a liquid preparation for oral administration may include a suspension, a liquid for internal use, an emulsion or a syrup, etc. In addition to commonly used simple diluents, such as water and liquid paraffin, various excipients, such as a wetting agent, a sweetener, an aroma, and a preservative, etc. may be included in the liquid preparation.

Examples of the preparation for parenterally administration include a sterilized aqueous solution, a non-aqueous solvent, a suspension solvent, an emulsion, a freeze-drying agent, and a suppository, etc. As the non-aqueous solvent and the suspension solvent, propylene glycol, polyethylene glycol, a vegetable oil such as an olive oil, an injectable ester such as ethylolate, etc. may be used. As a base for the suppository, witepsol, macrogol, tween 61, cacao butter, laurin butter, glycerol, gelatin, etc. may be used.

Considering that the pharmaceutical composition of the present invention is a composition for preventing or treating acute myeloid leukemia or metastatic breast cancer, it may be preferably administered parentally, for example, through an intravenous administration, an intraperitoneal administration, an intramuscular administration, a subcutaneous administration, a local administration, etc.

The indirubin derivative of the present invention may be used in the form of a pharmaceutically acceptable salt, and as the salt, an acid addition salt formed by a pharmaceutically acceptable free acid may be used. The acid addition salt is obtained from: inorganic acids, such as hydrochloric acid, nitric acid, phosphoric acid, sulfuric acid, hydrobromic acid, hydriodic acid, nitrous acid, or phosphorous acid; non-toxic organic acids, such as aliphatic mono and dicarboxylate, phenyl-substituted alkanoate, hydroxy alkanoate and alkane dioate, aromatic acids, and aliphatic and aromatic sulfonic acids; or organic acids, such as acetic acid, benzoic acid, citric acid, lactic acid, maleic acid, gluconic acid, methanesulfonic acid, 4-toluenesulfonic acid, tartaric acid, and fumaric acid. Examples of the pharmaceutically non-toxic salt include sulfate, pyrosulfate, bisulfate, sulfite, bisulfite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, sebacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, p-hydroxybutylate, glycolate, malate, tartrate, methanesulfonate, propanesulfonate, naphthalene-1-sulfonate, naphthalene-2-sulfonate, or mandelate, but are not limited thereto.

The acid addition salt according to the present invention may be prepared by a conventional method. For example, the acid addition salt may be prepared by dissolving the indirubin derivative of Chemical Formula 1 in an organic solvent, such as methanol, ethanol, acetone, methylene chloride, acetonitrile, etc., adding an organic acid or inorganic acid thereto to generate a precipitate, and then filtering and drying the generated precipitate, or may be prepared by distilling a solvent and an excess acid under reduced pressure, followed by drying or crystallizing in an organic solvent.

Additionally, a pharmaceutically acceptable metal salt may be prepared by using a base. For example, an alkali metal or alkaline earth metal salt is obtained by dissolving the compound in an excessive alkali metal hydroxide or alkaline earth metal hydroxide solution, filtering a non-soluble compound salt, and then evaporating and drying the filtrate. In particular, as the metal salt, a sodium, potassium, or calcium salt is appropriately prepared from a pharmaceutical aspect. Additionally, the corresponding silver salt is obtained by reacting an alkali metal or alkaline earth metal salt with a suitable silver salt (e.g., silver nitrate). Further, the present invention includes not only the indirubin derivative represented by Chemical Formula 1 and a pharmaceutically acceptable salt thereof, but also a solvate, a hydrate, a stereoisomer, etc., which may be prepared therefrom.

According to still another aspect of the present invention, the present invention provides a method for preventing or treating acute myeloid leukemia or metastatic breast cancer, including: (a) administering a composition including a compound represented by Chemical Formula 1 below, a pharmaceutically acceptable salt, a solvate, or a hydrate thereof to an individual:

istration route of the present invention may include various routes such as oral or parenteral administration as long as it can reach the target tissue. The formulation of the present invention may be prepared into various forms depending on the desired administration method.

According to still another aspect of the present invention, the present invention provides the use of a compound represented by Chemical Formula 1 below, a pharmaceutically acceptable salt, a solvate or a hydrate thereof, for the preparation of a pharmaceutical composition for preventing or treating acute myeloid leukemia or metastatic breast cancer:

[Chemical Formula 1]

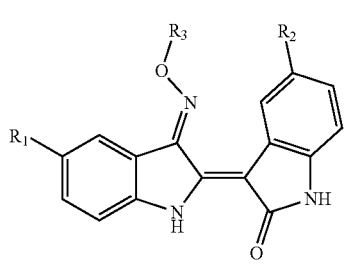

in the Chemical Formula 1, $R_1$ is hydrogen, fluoro, or hydroxy, $R_2$ is hydrogen, halogen, nitro, carboxyl, $C_1$-$C_4$ alkyl ester, or $C_1$-$C_4$ alkoxy substituted or unsubstituted with halogen, and $R_3$ is hydrogen, 2-bromoethyl,

[Chemical Formula 1]

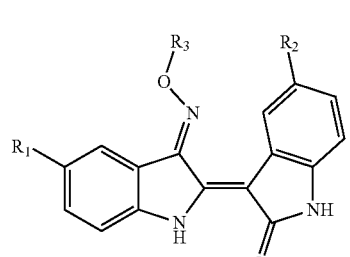

in the Chemical Formula 1, $R_1$ is hydrogen, fluoro, or hydroxy, $R_2$ is hydrogen, halogen, nitro, carboxyl, $C_1$-$C_4$ alkyl ester, or $C_1$-$C_4$ alkoxy substituted or unsubstituted with halogen, and R is hydrogen, 2-bromo ethyl,

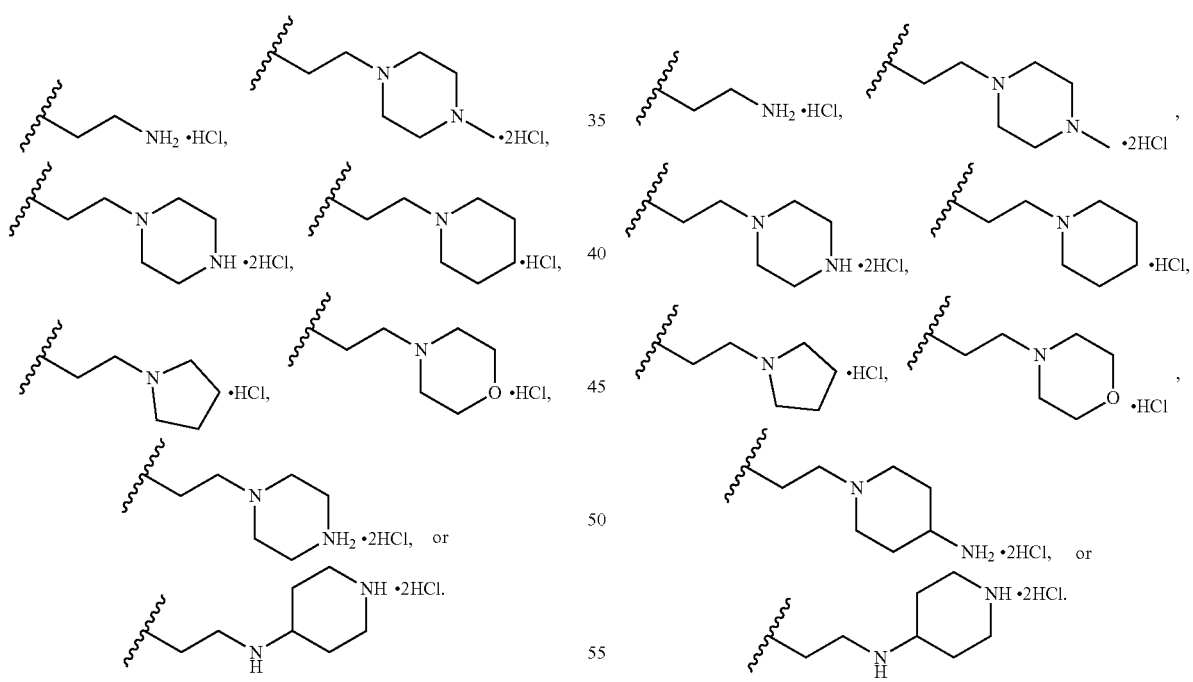

The terms used herein are as explained above. An individual to be administered with the formulation according to the present invention may refer to any animals, including humans. The animals may include humans as well as mammals such as cows, horses, sheep, pigs, goats, camels, antelopes, dogs, cats, etc., in need of treating similar symptoms, but are not limited thereto.

As used herein, the term "administration" refers to introducing the pharmaceutical composition of the present invention to a patient by any appropriate method, and the admin- Advantageous Effects The features and advantages of the present invention are summarized as follows:
 (a) The present invention provides a novel composition for inhibiting FLT3.
 (b) The present invention provides a pharmaceutical composition for preventing or treating acute myeloid leukemia or metastatic breast cancer.

(c) When the composition of the present invention is used, it can effectively inhibit the activity of FLT3 kinase, and can be usefully used to prevent or treat acute myeloid leukemia or metastatic breast cancer.

BRIEF DESCRIPTION OF DRAWINGS

FIG. 1 shows the structure and the inhibitory effect of LDD1937 (Compound 4) on the FLT3 kinase activity. (A) shows the chemical structure of LDD1937 and (B) shows the effect of LDD1937 on the FLT3 kinase activity in vitro. Inhibition of kinase activity of recombinant FLT3 was measured by HTRF analysis. The inhibition of kinase was calculated with 1% DMSO as a negative control. Data are the mean±SEM of three independent experiments.

FIG. 2 shows the in vivo anti-tumor efficacy of LDD1937 (Compound 4). MV-4-11 cells were inoculated subcutaneously into BALB/c nu/nu mice. When the tumor reached an average volume of 100 mm$^3$, mice were injected with 5 mg/kg or 10 mg/kg of LDD1937 or PBS (control) in the tail vein daily for 21 days. (A) shows the results of measuring the tumor size and calculating the tumor volume. (B) shows the result of measuring the tumor weight by sacrificing the mice at day 21 after drug administration. Representative images of a tumor mass dissected from the control group and the 5 mg/kg group were photographed (Inset). Data represent the mean±SEM. P<0.01, *P<0.001 compared to the control group, respectively.

FIG. 3 shows the change in body weight during the administration period of LDD1937. The weight of mice administered with 5 mg/kg or 10 mg/kg of LDD1937, or PBS (control) for 21 days from the start of the experiment was measured.

FIG. 4 shows the change in weight of the liver, kidney, and cancer tissue after administration of the four compounds for 4 weeks. LDD-2614 represents Compound 21, LDD-2633 represents Compound 28, LDD-2634 represents Compound 34, and LDD-2635 represents Compound 33.

FIG. 5 shows the change in volume of the cancer tissue after administration of the four compounds for 4 weeks. LDD-2614 represents Compound 21, LDD-2633 represents Compound 28, LDD-2634 represents Compound 34, and LDD-2635 represents Compound 33.

FIG. 6 shows the images of the size of cancer tissue after administration of the four compounds for 4 weeks. LDD-2614 represents Compound 21, LDD-2633 represents Compound 28, LDD-2634 represents Compound 34, and LDD-2635 represents Compound 33.

FIG. 7 shows the kinase selectivity profiles of Compound 33 (LDD-2635). (A) Chemical structure of LDD-2635. (B) shows biological activities of Compound 33 (LDD-2635) against FLT3 wild type and mutant kinases.

FIG. 8 shows the anticancer efficacy in MV4-11 xenograft mouse model of LDD-2635 and Compound 28 (LDD-2633). (n=10 for control group, n=6 for test group) BALB/c nude mice bearing MV4-11 tumor xenograft were treated once daily with each compound at 20 mg/kg or vehicle. (A) shows the relative tumor size of MV4-11 xenograft mouse model, (B) shows the body weight measurement of MV4-11 xenograft mice after oral administration of Compound 33 (LDD-2635) and Compound 28 (LDD-2633). (***, p<0.001)

DETAILED DESCRIPTION OF THE EMBODIMENTS

Hereinafter, the present invention will be described in further detail by way of Examples. However, these Examples are merely provided to specifically explain the present invention, and it is obvious to those skilled in the art that, according to the gist of the present invention, the scope of the present invention is not limited to these examples.

Example 1

Synthesis and Storage of Compounds

Compound 1 to Compound 47 were designed and synthesized.

1-1. Synthesis Diagram 1

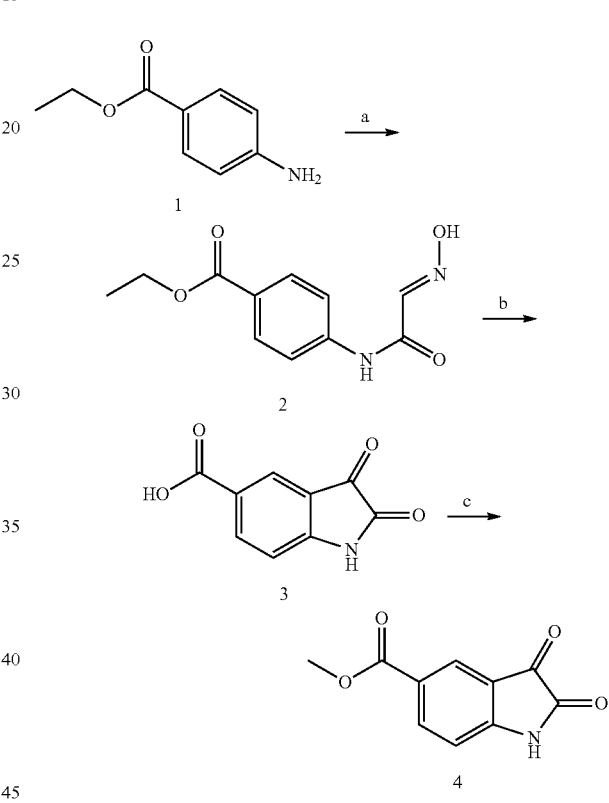

Reagents and Reaction conditions: (a) chloral hydrate, H$_2$NOH.HCl, Na$_2$SO$_4$, water, H$_2$SO$_4$, 100° C., on; (b) Conc. H$_2$SO$_4$, 90° C., 25 min; (c) H$_2$SO$_4$, 60° C., 1 hr.

Ethyl 4-aminobenzoate was heated in chloral hydrate and Na$_2$SO$_4$ aqueous solution for 1 hour. Subsequently, the resulting product was allowed to react with hydroxylamine hydrochloride and then cooled to obtain a solid product, which was filtered using diethyl ether to yield Product 2. The thus-obtained product was heated to 90° C. under a high concentration of sulfuric acid condition to obtain a product, which was neutralized with a 1N NaOH aqueous solution. Thereafter, the resulting product was extracted using EA and concentrated by rotary evaporation. The thus-obtained mixture was precipitated using a mixture of diethyl ether and DCM, and then filtered to yield Product 3. This product was allowed to react with sulfuric acid and methanol to obtain precipitates (Products 4a and 4b).

1-2. Synthesis Diagram 2

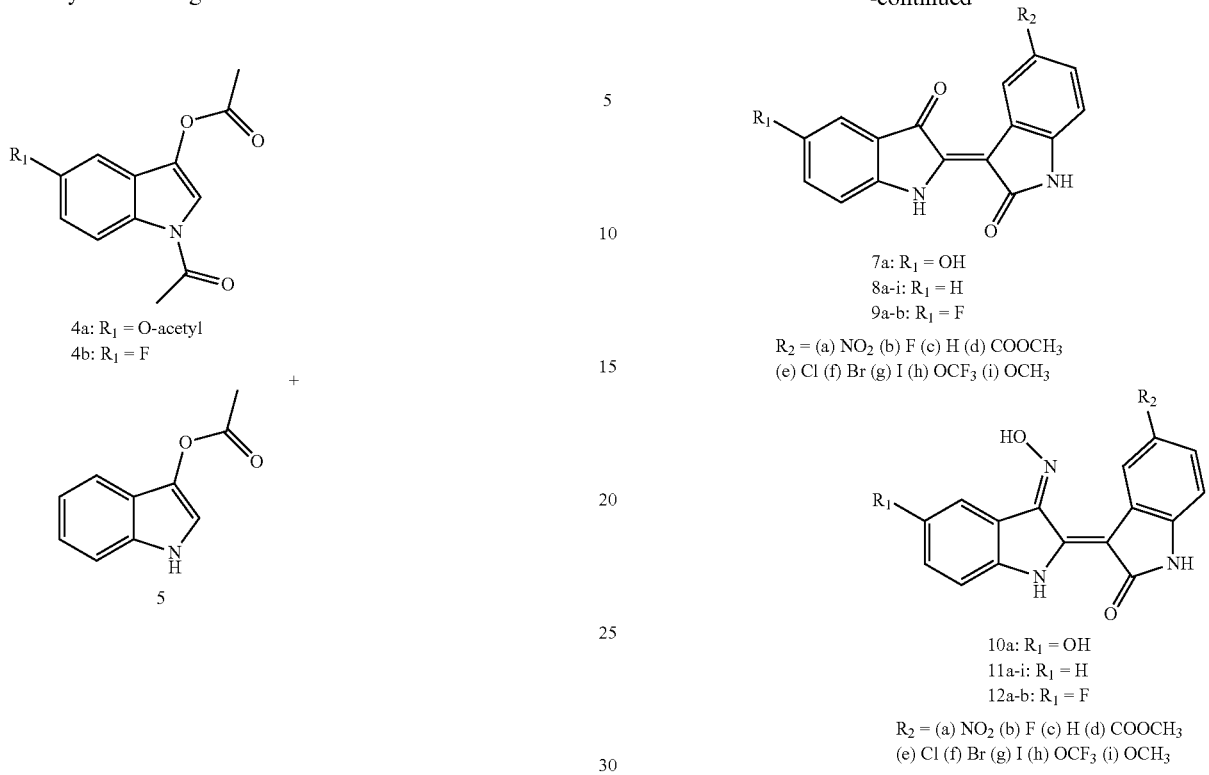

7a: $R_1$ = OH
8a-i: $R_1$ = H
9a-b: $R_1$ = F $R_2$ = (a) $NO_2$ (b) F (c) H (d) $COOCH_3$
(e) Cl (f) Br (g) I (h) $OCF_3$ (i) $OCH_3$

10a: $R_1$ = OH
11a-i: $R_1$ = H
12a-b: $R_1$ = F $R_2$ = (a) $NO_2$ (b) F (c) H (d) $COOCH_3$
(e) Cl (f) Br (g) I (h) $OCF_3$ (i) $OCH_3$

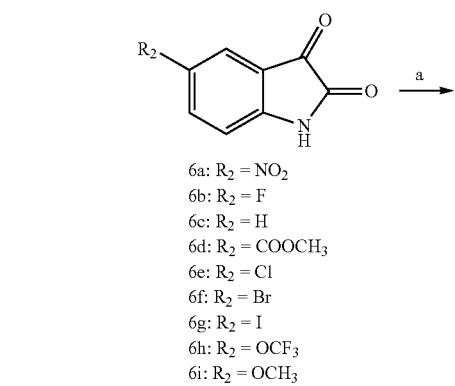

6a: $R_2$ = $NO_2$
6b: $R_2$ = F
6c: $R_2$ = H
6d: $R_2$ = $COOCH_3$
6e: $R_2$ = Cl
6f: $R_2$ = Br
6g: $R_2$ = I
6h: $R_2$ = $OCF_3$
6i: $R_2$ = $OCH_3$

Reagents and Reaction conditions: (a) $Na_2CO_3$, methanol:water(2:1), RT, 3 h (b) Hydroxylamine hydrochloride, pyridine, reflux, 6 h Isatin analogues 6a-i dissolved in MeOH were added to indoxyl N,O-diacetate 4a-b or indoxyl acetate 5, and the mixture was stirred for 5 minutes. Next, anhydrous $Na_2CO_3$ (2.5 eq) was added thereto and stirred at room temperature for 3 hours. Subsequently, the resulting product was filtered by adding water and washed several times with cold water to obtain Products 7a, 8a-i, and 9a-b in which 5,5' position was substituted in the form of precipitates. Thereafter, the thus-obtained products were dissolved in pyridine (0.1 M), added with hydroxylamine hydrochloride (5 eq) and refluxed for 6 hours. Then, the mixture was cooled and acidified with 1N HCl to yield precipitates, which were filtered and washed several times with water. Finally, the thus-obtained precipitates were purified through solidification using DCM and hexane to yield final Products 10a, 11a-i, and 12a-b.

1-3. Synthesis Diagram 3

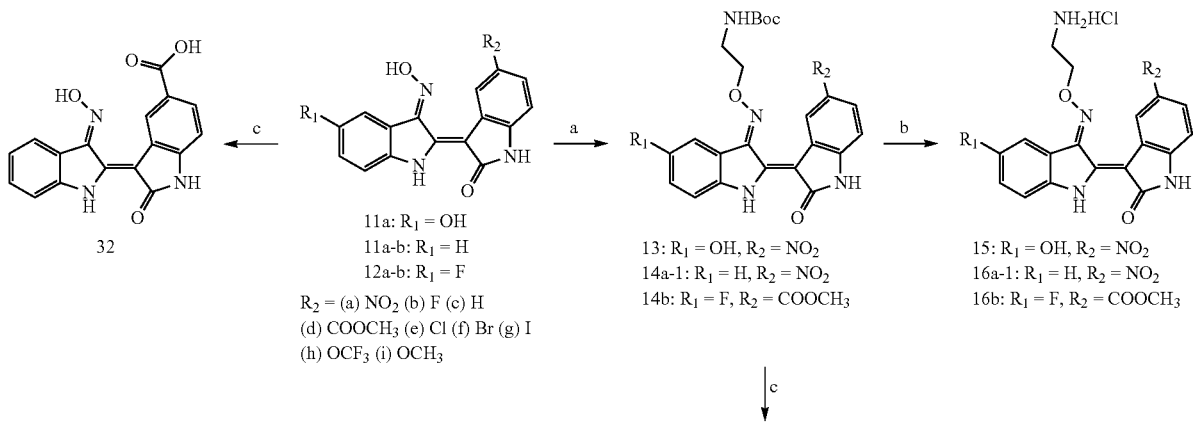

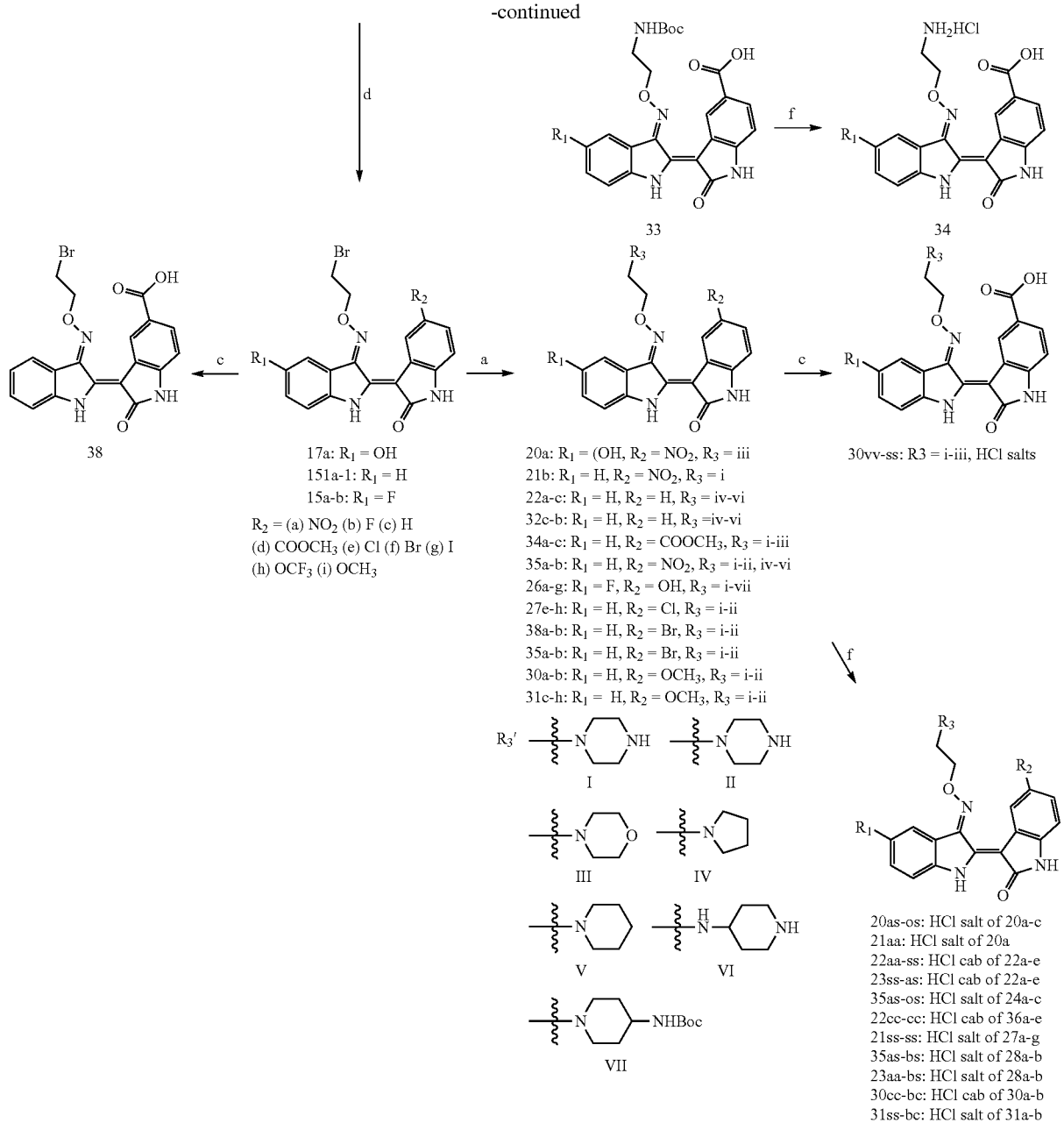

Reagents and Reaction conditions: (a) 2-(Boc-amino) ethyl bromide, K$_2$CO$_3$, DMF, RT, overnight; (b) 4N HCl in 1,4-dioxane, DCM, RT, 3 h; (c) 1N NaOH, 1,4-dioxane, 40° C., overnight (d) 1,2-dibromoethane, Et$_3$N, DMF, RT, overnight; (e) amines i-vi, DMF, 50° C., overnight; (f) 4N HCl in 1,4-dioxane, DCM or THF, 0° C., 30 min or TFA, 0° C., 30 min Representative synthesis methods for indinibin derivatives obtained by Synthesis Diagram 3 are as follows:

3-1) Alkyl Amination of Indirubin-3'-Oxime Derivatives

The representative synthesis method by alkyl amination of indirubin-3'-oxime derivatives obtained by Synthesis Diagram 3 is as follows:

Indirubin-3'-oxime derivatives were dissolved in DMF (1 ml to 4 ml), added with 2-(Boc-amino) ethyl bromide (1.2 eq) and K$_2$CO$_3$ (2 eq to 3 eq), and then stirred overnight at room temperature. After confirming that the reaction was completed, DMF was concentrated by rotary evaporation, and then water was added to generate precipitates, which were obtained through filtration. The precipitates were purified by column chromatography to yield indirubin derivative Products 13, 14a, and 14b. Next, the thus-obtained indinibin derivatives were dissolved in DCM (1 ml), added with 4N HCl in dioxane (6 eq to 18 eq) at 0° C. and stirred at room temperature for 3 hours. After confirming that the reaction was completed, the resulting precipitates were washed several times with DCM through filtration and dried to obtain as clean solid. The indirubin derivatives were obtained in the form of salts (Products 15, 16a, and 16b).

3-2) Alkylation of Indirubin-3'-Oxime Derivatives

The representative synthesis method by alkylation of indirubin-3'-oxime derivatives obtained by Synthesis Diagram 3 is as follows:

Indirubin-3'-oxime derivatives were dissolved in DMF (15 ml), added with 1,2-dibromoethane (10 eq) and TEA (3 eq to 10 eq), and then stirred overnight at room temperature. After confirming that the reaction was completed, water was added to generate precipitates, which were washed several times with water through filtration and dried to obtain as clean solid (Products 17a, 18a-i, and 19a-b). Next, the thus-obtained indinibin derivatives were dissolved in DMF, added with piperazine, morpholine, pyrrolidine, and piperidine reagents (10 eq to 30 eq), and then stirred at 50° C. overnight. After confirming that the reaction was completed, water was added to the mixed solution to generate solid, which was obtained through filtration and washed several times with water. Thereafter, the remaining impurities were washed with acetone and MeOH to obtain desired products (Products 20a-c, 21a, 22a-e, 23a-e, 24a-c, 25a-d, 26a-g, 27a-b, 28a-b, 29a-b, 30a-b, and 31a-b). Next, the thus-obtained products were dissolved in DCM or THF, added with 4N HCl in dioxane at 0° C., and then stirred for 30 minutes. After the reaction, the resulting solid was washed with DCM by filtration to obtain desired products in the form of salts (Products 20as-cs, 21as, 22as-es, 23as-es, 24as-cs, 25as-ds, 26as-fs, 27as-bs, 28as-bs, 29as-bs, 30as-bs, and 31as-bs). Further, Compound 26gs was obtained in the form of a salt in the same manner using TFA.

3-3) Indirubin-3'-Oxime Carboxylic Acid Derivatives

The representative synthesis method for indirubin-3'-oxime carboxylic acid derivatives obtained by Synthesis Diagram 3 is as follows:

Indirubin-3'-oxime derivatives (Products 11d, 14b, 18d, and 24a-24c) were dissolved in 1,4-dioxane, added with 1N NaOH, and then stirred overnight at 40° C. After confirming that the reaction was completed, the resulting product was cooled at room temperature and acidified by adding 1N HCl. Thereafter, water was concentrated and the remaining NaCl after concentration was removed through filtration using MeOH to obtain desired products as solid (Products 32, 33, 35, and 3 las-cs (salt)). Then, the thus-obtained Product 33 was dissolved in DCM, added with 4N HCl in dioxane at 0° C., and then stirred for 10 minutes. After the reaction, the resulting solid was washed with DCM by filtration to obtain the desired Product 34 in the form of a salt.

Confirmation of Synthesis of Compounds

Product 11d: Methyl (2Z,3E)-3-(hydroxyimino)-2'-oxo-[2,3'-biindolinylidene]-5'-carboxylate (Compound 1, LDD-1075)

$^1$H NMR (400 MHz, DMSO-d6) δ ppm 11.76-11.80 (m, 1H), 11.05-11.10 (m, 1H), 9.17-9.21 (m, 1H), 8.24 (d, J=8.01 Hz, 1H), 7.73-7.78 (m, 1H), 7.36-7.42 (m, 2H), 7.00-7.06 (m, 1H), 6.92-6.98 (n, 1H), 3.79-3.86 (n, 3H).

Product 18d: Methyl (2Z,3E)-3-((2-bromoethoxy)imino)-2'-oxo-[2,3'-biindolinylidene]-5'-carboxylate (Compound 2, LDD-1916)

$^1$H NMR (400 MHz, DMSO-d6) δ ppm 11.68 (s, 1H), 11.18 (s, 1H), 9.36 (d, J=1.6 Hz, 1H), 8.23 (d, J=7.6 Hz, 1H), 7.83 (dd, J=8.0, 1.6 Hz, 1H), 7.48 (m, 2H), 7.10 (m, 1H), 7.01 (d, J=8.0 Hz, 1H), 4.98 (t, J=5.6 Hz, 2H), 4.06 (t, J=5.6 Hz, 2H), 3.86 (s, 3H).

Product 1613: Methyl (2Z,3E)-3-((2-aminoethoxy)imino)-2'-oxo-[2,3'-biindolinylidene]-5'-carboxylate hydrochloride (Compound 3, LDD-1918)

$^1$H NMR (400 MHz, DMSO-d6) δ ppm 11.66 (s, 1H), 11.18 (s, 1H), 9.30 (d, J=1.60 Hz, 1H), 8.24 (d, 1-7.78 Hz, 1H), 8.17 (brs, 2H), 7.80 (dd, J=8.13, 1.72 Hz, 1H), 7.41-7.48 (m, 2H), 7.04 (ddd, J=7.90, 5.72, 2.63 Hz, 1H), 6.98 (d, J=8.01 Hz, 1H), 4.78-4.85 (m, 2H), 3.79-3.86 (m, 3H), 3.47 (d, J=4.81 Hz, 2H).

Product 24as: Methyl (2Z,3E)-2'-oxo-3-((2-(piperazin-1-yl)ethoxy)imino)-[2,3'-biindolinylidene]-5'-carboxylate dihydrochloride (Compound 4, LDD1937)

$^1$H NMR (400 MHz, DMSO-d6) δ ppm 11.70 (s, 1H), 11.23 (s, 1H), 9.36 (s, 1H), 8.27 (d, J=7.6 Hz, 1H), 7.84 (d, J=8.4 Hz, 1H), 7.48 (m, 2H), 7.07 (m, 1H), 7.02 (d, J=8.8 Hz, 1H), 5.03 (m, 2H), 3.88 (s, 3H), 3.30 (m, 10H, overlapped with DMSO).

Product 24bs: Methyl (2Z,3E)-3-((2-(4-methylpiperazin-1-yl)ethoxy)imino)-2'-oxo-[2,3'-biindolinylidene]-5'-carboxylate dihydrochloride (Compound 5, LDD-1938) $^1$H NMR (400 MHz, DMSO-d6) δ ppm 11.71 (s, 1H), 11.22 (s, 1H), 9.38 (d, J=1.6 Hz, 1H), 8.24 (d, J=7.6 Hz, 1H), 7.84 (dd, J=8.4, 1.6 Hz, 1H), 7.48 (m, 2H), 7.08 (m, 1H), 7.02 (d, J=8.4 Hz, 1H), 4.96 (m, 2H), 3.87 (s, 3H), 3.30 (m, 10H, overlapped with water).

Product 24cs: Methyl (2Z,3E)-3-((2-morpholinoethoxy)imino)-2'-oxo-[2,3'-biindolinylidene]-5'-carboxylate hydrochloride (Compound 6, LDD-1943)

$^1$H NMR (400 MHz, DMSO-d6) δ11.70 (s, 1H), 11.22 (s, 1H), 10.94 (brs, 1H, morpholine N+−H), 9.36 (s, 1H), 8.26 (d, J=7.6 Hz, 1H), 7.84 (dd, J=8.0, 2.0 Hz, 1H), 7.49 (m, 2H), 7.09 (m, 1H), 7.02 (d, J=8.0 Hz, 1H), 5.08 (brs, 2H), 3.97 (m, 2H), 3.80 (s, 3H), 3.81 (m, 4H), 3.56 (m, 2H), 3.18 (m, 2H, partially overlapped with water).

Product 32: (2Z,3E)-3-(hydroxyimino)-2'-oxo-[2,3'-biindolinylidene]-5'-carboxylic acid (Compound 7, LDD-1076)

$^1$H NMR (400 MHz, DMSO-d6) δ ppm 11.68 (s, 1H), 11.23 (s, 1H), 8.73-8.78 (m, 1H), 8.18 (s, 1H), 8.01 (d, J=5.04 Hz, 1H), 7.49 (m, 2H), 6.95 (d, J=8.0 Hz, 1H).

Product 35: (2Z,3E)-3-((2-bromoethoxy)imino)-2'-oxo-[2,3'-biindolinylidene]-5'-carboxylic acid (Compound 8, LDD-1939)

$^1$H NMR (400 MHz, DMSO-d6) δ ppm 11.66 (s, 1H), 11.11 (s, 1H), 9.34 (s, 1H), 8.22 (d, J=7.6 Hz, 1H), 7.80 (d, J=8.0 Hz, 1H), 7.63 (m, 2H), 7.08 (m, 1H), 6.97 (d, J=8.4 Hz, 1H), 4.96 (t, J=5.6 Hz, 2H), 4.03 (t, J=5.6 Hz, 2H).

Product 34: (2Z,3E)-3-((2-aminoethoxy)imino)-2'-oxo-[2,3'-biindolinylidene]-5'-carboxylic acid hydrochloride (Compound 9, LDD-1936)

$^1$H NMR (400 MHz, DMSO-d6) δ ppm 11.68 (s, 1H), 11.18 (s, 1H), 9.35 (d, J=1.2 Hz, 1H), 8.26 (d, J=7.6 Hz, 1H), 8.17 (s, 3H, H+), 7.82 (dd, J=8.0, 1.6 Hz, 1H), 7.48 (m, 2H), 7.08 (m, 1H), 7.00 (d, J=8.4 Hz, 1H), 4.83 (t, J=5.2 Hz, 2H), 3.45 (t, J=5.2 Hz, 2H).

Product 36as: (2Z,3E)-2'-oxo-3-((2-(piperazin-1-yl)ethoximino)-[2,3'-biindolinylidene]-5'-carboxylic acid dihydrochloride (Compound 10, LDD-1940)

$^1$H NMR (400 MHz, DMSO-d6) δ ppm 11.69 (s, 1H), 11.17 (s, 1H), 9.37 (s, 1H), 8.91 (brs, 2H, piperazine N+−H), 8.23 (d, J=7.6 Hz, 1H), 7.82 (d, J=8.4 Hz, 1H), 7.47 (m, 2H), 7.07 (m, 1H), 7.00 (d, J=8.4 Hz, 1H), 4.92 (brs, 2H), 3.05 (m, 10H, overlapped with water).

Product 36bs: (2Z,3E)-3-((2-(4-methylpiperazin-1-yl)ethoxy)imino)-2'-oxo-[2,3'-biindolinylidene]-5'-carboxylic acid dihydrochloride (Compound 11, LDD-1941)

$^1$H NMR (400 MHz, DMSO-d6) δ ppm 11.68 (s, 1H), 11.16 (s, 1H), 9.36 (s, 1H), 8.23 (d, J=8.0 Hz, 1H), 7.82 (d, J=8.0 Hz, 1H), 7.47 (m, 2H), 7.07 (m, 1H), 6.99 (d, J=8.0 Hz, 1H), 4.93 (brs, 2H), 3.17 (m, 10H, overlapped with water), 2.77 (s, 3H).

Product 36cs: (2Z,3E)-3-((2-morpholinoethoxy)imino)-2'-oxo-[2,3'-biindolinylidene]-5'-carboxylic acid hydrochloride (Compound 12, LDD-1944)

$^1$H NMR (400 MHz, DMSO-d6) δ ppm 11.67 (s, 1H), 11.27 (brs, 1H, morpholine N+–H), 11.18 (s, 1H), 9.34 (s, 1H), 8.25 (d, J=7.6 Hz, 1H), 7.82 (d, J=8.4 Hz, 1H), 7.48 (m, 2H), 7.08 (m, 1H), 6.99 (d, J=8.0 Hz, 1H), 5.06 (brs, 2H), 3.96 (m, 2H), 3.80 (m, 4H), 3.53 (m, 2H), 3.24 (m, 2H, partially overlapped with water).

Product 10a: (2Z,3E)-5-hydroxy-3-(hydroxyimino)-5'-nitro-[2,3'-biindolinylidene]-2'-one (Compound 13, LDD-963)

$^1$H NMR (300 MHz, DMSO-d6) δ 13.87 (1H, s, NOH), 11.78 (1H, s, NH), 11.35 (1H, s, N–H), 9.41 (1H, d, J=2.8 Hz), 9.32 (1H, s, O–H), 8.05 (1H, dd, J=11.6, 2.8 Hz), 7.76 (1H, d, J=3.2 Hz), 7.29 (1H, d, J=11.6 Hz), 7.04 (1H, d, J=11.2 Hz) 6.86 (1H, dd, J=11.2, 3.2 Hz)

Product 20bs: (2Z,3E)-5-hydroxy-3-((2-(4-methylpiperazin-1-yl)ethoxy)imino)-5'-nitro-[2,3'-biindolinylidene]-2'-one dihydrochloride (Compound 14, LDD-1893)

$^1$H NMR (400 MHz, DMSO-d6) δ 11.65 (s, 1H), 11.45 (s, 1H), 9.55-9.48 (m, 2H), 8.10-8.07 (dd, J=8.48, 2.32 Hz, 1H), 7.74 (s, 1H), 7.32-7.30 (d, J=8.48 Hz, 1H), 7.08-7.06 (d, J=8.48 Hz, 1H), 6.93-6.91 (dd, J=8.48, 2.52 Hz, 1H), 5.00 (m, 2H), 3.45-3.11 (m, 10H, overlapped with water peak), 2.79 (s, 3H).

Product 16a: (2Z,3E)-3-((2-aminoethoxy)imino)-5'-nitro-[2,3'-biindolinylidene]-2'-one hydrochloride (Compound 15, LDD-2365) $^1$H NMR (400 MHz, DMSO-d6) δ 11.66 (s, 1H) 11.18 (s, 1H) 9.30 (d, J=1.60 Hz, 1H) 8.24 (d, J=7.78 Hz, 1H) 8.17 (br. s., 2H) 7.80 (dd, J=8.13, 1.72 Hz, 1H) 7.41-7.48 (m, 2H) 7.04 (ddd, J=7.90, 5.72, 2.63 Hz, 1H) 6.98 (d, J=8.01 Hz, 1H) 4.78-4.85 (m, 2H) 3.79-3.86 (m, 3H) 3.47 (d, J=4.81 Hz, 2H)

Product 21as: (2Z,3E)-5'-nitro-3-((2-(piperazin-1-yl)ethoxy)imino)-[2,3'-biindolinylidene]-2'-one dihydrochloride (Compound 16, LDD-2366)

$^1$H NMR (400 MHz, D$_2$O) δ 8.22 (s, 1H), 7.38 (d, J=7.32 Hz, 1H), 7.30-7.27 (dd, J=8.32, 1.48 Hz, 1H), 7.09-7.05 (t, J=7.80 Hz, 1H), 6.77-6.73 (t, J=7.32 Hz, 1H), 6.49-6.47 (d, J=7.80 Hz, 1H), 6.17 (d, J=8.32 Hz, 1H), 4.33 (m, 2H), 3.47-3.36 (m, 10H).

Product 15as: (2Z,3E)-5-fluoro-5'-nitro-3-((2-(piperazin-1-yl)ethoxy)imino)-[2,3'-biindolinylidene]-2'-one dihydrochloride (Compound 17, LDD-2612)

$^1$H NMR (500 MHz, D$_2$O) δ 8.14 (s, 1H), 7.31 (d, J=8 Hz, 1H), 7.06 (d, J=8 Hz 1H), 6.77 (m, 1H), 6.43 (m, 1H), 6.14 (d, J=8.5 Hz, 1H), 4.41 (brs, 2H), 3.52 3.44 (m, 10H).

Product 25bs: (2Z,3E)-5-fluoro-3-((2-(4-methylpiperazin-1-yl)ethoxy)imino)-5'-nitro-[2,3'-biindolinylidene]-2'-one dihydrochloride (Compound 18, LDD-2613)

$^1$H NMR (400 MHz, DMSO-d6) δ 9.54 (d, J=2.1 Hz, 1H), 8.09 (m, 1H), 7.95 (dd, J=8.9, 2.4 Hz, 1H), 7.45 (m, 1H), 7.31 (m, 1H), 7.08 (d, J=8.88 Hz, 1H), 4.97 (brs, 2H), 3.40 (m, 10H, partially overlapped with water), 2.80 (s, 3H). $^1$H NMR (400 MHz, D$_2$O) δ 8.28 (s, 1H), 7.38-7.36 (d, J=8.4 Hz, 1H), 7.01-6.99 (d, J=8.4 Hz, 1H), 6.79 (m, 1H), 6.48-6.45 (m, 1H), 6.26-6.24 (d, J=7.6 Hz, 1H), 4.27 (brs, 2H), 3.58-3.05 (m, 10H), 2.80 (s, 3H).

Product 25ds: (2Z,3E)-5-fluoro-5'-nitro-3-((2-(piperidin-1-yl)ethoxy)imino)-[2,3'-biindolinylidene]-2'-one hydrochloride (Compound 19, LDD-2835)

$^1$H NMR (400 MHz, DMSO-d6) δ (ppm); 11.80 (m, 1H), 10.79 (s, 1H), 8.46 (dd, J=11.3, 2.4 Hz, 1H), 8.19 (m, 1H), 7.48 (m, 2H), 7.08 (m, 1H), 7.01 (m, 1H), 6.90 (m, 1H), 4.69 (t, J=6.1 Hz, 2H), 2.90 (m, 2H), 2.24 (s, 2H), 1.94 (m, 1H), 1.58 (m, 3H), 1.40 (m, 2H)

Product 25cs: (2Z,3E)-5-fluoro-5'-nitro-3-((2-(pyrrolidin-1-yl)ethoxy)imino)-[2,3'-biindolinylidene]-2'-one hydrochloride (Compound 20, LDD-2836)

$^1$H NMR (400 MHz, DMSO-d6) δ (ppm); 9.56 (s, 1H), 8.07 d, J=8.8 Hz, 1H), 7.88 (d, J=8.8 Hz, 1H), 7.48 (s, 1H), 7.34 (s, 1H), 7.03 (d, J=9.6 Hz, 1H), 4.84 (m, 2H), 4.12 (m, 2H).

Product 26as: (2Z,3E)-5,5'-difluoro-3-((2-(piperazin-1-yl)ethoxy)imino)-[2,3'-biindolinylidene]-2'-one dihydrochloride (Compound 21, LDD-2614)

$^1$H NMR (400 MHz, D$_2$O)) δ 7.31 (d, J=9.6 Hz, 1H), 7.02 (d, J=6.4 Hz, 1H), 6.77 (t, J=6.8 Hz, 1H), 6.48-6.42 (m, 2H), 6.22-6.19 (m, 1H), 4.50 (m, 2H), 3.46-3.43 (m, 10H).

Product 26bs: (2Z,3E)-5,5'-difluoro-3-((2-(4-methylpiperazin-1-yl)ethoxy)imino)-[2,3'-biindolinylidene]-2'-one dihydrochloride (Compound 22, LDD-2615)

$^1$H NMR (500 MHz, DMSO-d$_6$) δ 11.75 (s, 1H), 10.85 (s, 1H), 8.33 (d, J=11 Hz, 1H), 8.06 (m, 1H), 7.46 (m, 1H), 7.36 (m 1H), 7.00 (m, 1H) 6.89 (m, 1H), 4.97 (m, 2H), 3.54 3.10 (m, 10H, partially overlapped with water), 2.80 (s, 3H).

Product 26es: (2Z,3E)-5,5'-difluoro-3-((2-(piperidin-1-yl)ethoxy)imino)-[2,3'-biindolinylidene]-2'-one hydrochloride (Compound 23, LDD-2766)

$^1$H NMR (500 MHz, DMSO-d$_6$) δ 11.74 (s, 1H), 10.84 (s, 1H), 10.21 (brs, 1H), 8.33-8.30 (dd, J=11, 2.5 Hz, 1H), 8.03-8.00 (dd, J=8.5, 2.5 Hz, 1H), 7.49-7.46 (dd, J=9, 4.5 Hz, 1H), 7.38-7.35 (td, J=9, 2.5 Hz, 1H), 7.01-6.97 (td, J=8.5, 3 Hz, 1H), 6.89-6.86 (dd, J=8.5, 4.5 Hz, 1H), 5.02-4.99 (t, J=4.5 Hz, 2H), 3.70 (m, 2H), 3.60-3.58 (t, J=6.5 Hz, 1H), 3.56-3.52 (m, 2H), 3.07-3.44 (t, J=12.5 Hz, 2H), 1.76-1.65 (m, 5H).

Product 26ds: (2Z,3E)-5,5'-difluoro-3-((2-(pyrrolidin-1-yl)ethoxy)imino)-[2,3'-biindolinylidene]-2'-one hydrochloride (Compound 24, LDD-2770)

$^1$H NMR (600 MHz, DMSO-d6) δ 11.76 (s, 1H), 10.85 (s, 1H), 10.25 (brs, 1H), 8.34-8.32 (dd, J=11.4, 2.4 Hz, 1H), 8.06-8.04 (dd, J=8.4, 2.4 Hz, 1H), 7.50-7.48 (q, J=4.2 Hz, 1H), 7.40-7.36 (td, J=9, 2.4 Hz, 1H), 7.03-6.98 (td, J=9, 3 Hz, 1H), 6.90-6.87 (q, J=4.2 Hz, 1H), 4.95 (t, J=4.8 Hz, 2H), 3.82 (q, J=5.04 Hz, 2H), 3.69-3.58 (m, 2H), 3.17-3.11 (m, 2H), 2.03-1.99 (m, 2H), 1.90-1.86 (m, 2H).

Product 26gs: (2Z,3E)-3-((2-(4-aminopiperidin-1-yl)ethoxy)imino)-5,5'-difluoro-[2,3'-biindolinylidene]-2'-one dihydrochloride (Compound 25, LDD-2853)

$^1$H NMR (400 MHz, DMSO-d6) δ (ppm); 8.32 (dd, J=11.1, 2.6 Hz, 1H), 8.01 (dd, J=8.7, 2.6 Hz, 1H), 7.48 (d, J=8.9, 4.6 Hz, 1H), 7.40 (m, 1H), 7.04 (m, 1H), 6.88 (dd, J=8.6, 4.9 Hz, 1H), 5.01 (m, 2H), 3.37 (m, 4H), 2.96 (dd, J=11.6 Hz, 2H), 2.15 (m, 4H), 1.73 (m, 1H).

Product 26fs: (2Z,3E)-5,5'-difluoro-3-((2-(piperidin-4-ylamino)ethoxy)imino)-[2,3'-biindolinylidene]-2'-one dihydrochloride (Compound 26, LDD-2767)

$^1$H NMR (500 MHz, D$_2$O) δ 7.27-7.25 (d, J=10.5 Hz, 1H), 6.98-6.97 (d, J=7 Hz, 1H), 6.65-6.62 (t, J=6.5 Hz, 1H), 6.44-6.42 (t, J=7.5 Hz, 1H), 6.32 (dd, J=8, 3.5 Hz, 1H), 6.18 6.15 (dd, J=8.5, 5 Hz, 1H), 4.43 (m, 2H), 3.62-3.29 (m, 5H), 3.01-2.96 (t, J=13 Hz, 2H), 2.32-2.29 (d, J=13.5 Hz, 1H), 1.86-1.79 (dd, J=13, 3 Hz, 2H).

Product 26es: (2Z,3E)-5,5'-difluoro-3-((2-morpholinoethoxy)imino)-[2,3'-biindolinylidene]-2'-one hydrochloride (Compound 27, LDD-2834)

$^1$H NMR (400 MHz, DMSO-d$_6$) δ 11.70 (s, 1H), 11.20 (brs, 1H), 10.81 (s, 1H), 8.29 8.26 (dd, J=11.6, 2.8 Hz, 1H), 8.02-7.99 (dd, J=8.4, 2.4 Hz, 1H), 7.45-7.42 (dd, J=8.4, 4.4 Hz, 1H), 7.35-7.32 (td, J=9.2, 2.8 Hz, 1H), 6.96-6.93 (td, J=8.8, 2.8 Hz, 1H), 6.85-6.82 (dd, J=8, 4.8 Hz, 1H), 5.00 (m, 2H), 3.95-3.92 (m, 2H), 3.79-3.76 (m, 3H), 3.51-3.49 (m, 2H), 3.24-3.22 (m, 3H, partially overlapped with water).

Product 23as: (2Z,3E)-3-((2-(piperazin-1-yl)ethoxy)imino)-[2,3'-biindolinylidene]-2'-one dihydrochloride (Compound 28, LDD-2633)

$^1$H NMR (400 MHz, DMSO-d$_6$) δ 11.65 (s, 1H), 10.78 (s, 1H), 8.56 (d, J=7.8 Hz, 1H), 8.17 (m, 1H), 7.42 (m, 2H), 7.13 (t, J=7.6 Hz, 1H), 6.99 (m, 2H), 6.88 (d, J=7.84 Hz, 1H), 4.8 (m, 2H), 3.20-2.60 (m, 10H, overlapped in water peak).

Product 23bs: (2Z,3E)-3-((2-(4-methylpiperazin-1-yl)ethoxy)imino)-[2,3'-biindolinylidene]-2'-one dihydrochloride (Compound 29, LDD-2632)

$^1$H NMR (400 MHz, D$_2$O) δ 7.73 (d, J=7.80 Hz, 1H), 7.44 (d, J=7.80 Hz, 1H), 7.04 (t, J=8.24 Hz, 1H), 6.85 (t, J=7.32 Hz, 1H), 6.71-6.64 (m, 2H), 6.52-6.46 (m, 2H), 4.33 (m, 2H), 3.48-3.37 (m, 10H), 2.84 (s, 3H).

Product 23 ds: (2Z,3E)-3-((2-(piperidin-1-yl)ethoxy)imino)-[2,3'-biindolinylidene]-2'-one hydrochloride (Compound 30, LDD-2870)

$^1$H NMR (400 MHz, DMSO-d$_6$) δ 11.65 (s, 1H), 10.79-10.76 (m, 2H), 8.53 (d, J=7.80 Hz, 1H), 8.17 (d, J=7.80 Hz, 1H), 7.44-7.37 (m, 2H), 7.15-7.11 (td, J=8.24, 0.92 Hz, 1H), 7.02-6.97 (m, 2H), 6.88 (d, J=7.76 Hz, 1H), 5.01 (t, J=5.04, 2H), 3.63-3.59 (q, J=5.04 Hz, 2H). 3.52-3.45 (m, 2H), 3.05-2.98 (m, 2H), 1.79-1.61 (m, 5H), 1.39-1.28 (m, 1H).

Product 23cs: (2Z,3E)-3-((2-(pyrrolidin-1-yl)ethoxy)imino)-[2,3'-biindolinylidene]-2'-one hydrochloride (Compound 31, LDD-2872)

$^1$H NMR (400 MHz, DMSO-d$_6$) δ 11.66 (s, 1H), 10.79 (brs, 2H), 8.52 (d, J=7.6 Hz, 1H), 8.20 (d, J=7.6 Hz, 1H), 7.45-7.38 (m, 2H), 7.16-7.11 (t, J=8 Hz, 1H), 7.03-6.97 (m, 2H), 6.89-6.87 (d, J=8 Hz, 1H), 4.94 (m, 2H), 3.73-3.71 (m, 2H), 3.60-3.53 (m, 2H), 3.09-3.05 (t, J=8 Hz, 2H), 2.05-1.70 (m, 4H).

Product 23es: (2Z,3E)-3-((2-(piperidin-4-ylamino)ethoxy)imino)-[2,3'-biindolinylidene]-2'-one dihydrochloride (Compound 32, LDD-2871)

$^1$H NMR (400 MHz, DMSO-d$_6$) δ 11.64 (s, 1H), 10.81 (s, 1H), 8.50 (d, J=4.12 Hz, 1H), 8.45 (m, 2H), 8.18 (d, J=7.76 Hz, 1H), 7.42-7.34 (m, 2H), 7.14-7.11 (t, J=7.80 Hz, 1H), 7.01-6.97 (m, 1H), 5.14 (m, 2H), 3.70-3.12 (m, 7H, partially overlapped with water), 2.12-1.99 (m, 4H).

Product 22as: (2Z,3E)-5'-fluoro-3-((2-(piperazin-1-yl)ethoxy)imino)-[2,3'-biindolinylidene]-2'-one dihydrochloride (Compound 33, LDD-2635)

$^1$H NMR (400 MHz, DMSO-d$_6$) δ 11.74 (s, 1H), 10.90 (s, 1H), 10.17 (m, 2H), 8.34-8.31 (dd, J=11.2, 2.96 Hz, 1H), 8.29 (d, J=7.80 Hz, 1H), 7.45-7.43 (m, 2H), 7.04 (t, J=7.32 Hz, 1H), 7.01-6.95 (m, 1H), 6.91-6.87 (m, 1H), 5.04 (m, 2H), 3.85 (m, 2H, overlapped in solvent peak), 3.78-3.52 (m, 4H), 3.48 (m, 4H). $^{13}$C NMR (100 MHz, DMSO-d6) δ 171.26, 153.06, 146.26, 144.97, 135.64, 133.88, 129.58, 123.68, 122.54, 116.38, 113.18, 112.93, 112.55, 110.59, 109.93, 100.85, 71.34, 54.48, 48.70, the other peak is overlapped in solvent peak. $^{13}$C NMR (100 MHz, D$_2$O) δ 170.75, 156.54, 151.78, 144.67, 144.12, 132.99, 128.19, 122.07, 122.05, 117.52, 115.26, 110.70, 110.66, 109.32, 109.24, 97.62, 69.80, 55.55, 49.17, 40.78. LC/MS (ESI, m/z) 408.18 [M−Cl]+. HRMS (FAB) m/z calculated for C22H23FN5O5 [M−Cl]+408.1836, found 408.1834.

Product 22bs: (2Z,3E)-5'-fluoro-3-((2-(4-methylpiperazin-1-yl)ethoxy)imino)-[2,3'-biindolinylidene]-2'-one dihydrochloride (Compound 34, LDD-2634)

$^1$H NMR (400 MHz, D$_2$O) δ 7.21-7.18 (d, J=7.32 Hz, 1H), 7.05-7.02 (dd, J=11.6, 2.44 Hz, 1H) 6.95-6.92 (t, J=7.32 Hz, 1H), 6.59-6.55 (t, J=7.32 Hz, 1H), 6.36-6.34 (d, J=7.84 Hz, 1H), 6.21-6.16 (m, 1H), 5.92-5.88 (m, 1H), 4.20 (m, 2H), 3.60-3.41 (m, 8H), 3.35 (m, 2H), 2.92 (s, 3H).

Product 22ds: (2Z,3E)-5'-fluoro-3-((2-(piperidin-1-yl)ethoxy)imino)-[2,3'-biindolinylidene]-2'-one hydrochloride (Compound 35, LDD-2768)

$^1$H NMR (400 MHz, DMSO-d$_6$) δ 11.76 (s, 1H), 10.86 (s, 1H), 10.64 (brs, 1H), 8.37-8.34 (d, J=11.2 Hz, 1H), 8.26-8.21 (d, J=7.2 Hz, 1H), 7.46 (m, 2H), 7.08-6.97 (in, 2H), 6.90-6.86 (m, 1H), 5.03 (brs, 2H), 3.69 (m, 2H), 3.54-3.52 (d, J=11.6 Hz, 2H), 3.06 (m, 2H), 1.79-1.67 (m, 5H), 1.38 (m, 1H).

Product 22cs: (2Z,3E)-5'-fluoro-3-((2-(pyrrolidin-1-yl)ethoximino)-[2,3'-biindolinylidene]-2'-one hydrochloride (Compound 36, LDD-2771)

$^1$H NMR (400 MHz, DMSO-d$_6$) δ 11.73 (s, 1H), 10.82 (s, 1H), 10.59 (brs, 1H), 8.35-8.32 (d, J=10.4 Hz, 1H), 8.22-8.19 (d, J=7.2 Hz, 1H), 7.43 (m, 2H), 7.03-6.94 (m, 2H), 6.85 (m, 1H), 4.92 (m, 2H), 3.77 (m, 2H), 3.60-3.56 (m, 2H), 3.09 (m, 2H), 1.97-1.72 (in, 4H).

Product 22es: (2Z,3E)-5'-fluoro-3-((2-(piperidin-4-ylamino)ethoxy)imino)-[2,3'-biindolinylidene]-2'-one dihydrochloride (Compound 37, LDD-2769)

$^1$H NMR (500 MHz, D$_2$O) δ 7.48-7.46 (d, J=8 Hz, 1H), 7.42-7.39 (d, J=12 Hz, 1H), 7.05-7.01 (t, J=7.5 Hz, 1H), 6.70-6.67 (t, J=7.5 Hz, 1H), 6.51-6.48 (d, J=7.5 Hz, 1H), 6.47-6.43 (m, 1H), 6.23-6.20 (dd, J=8, 5 Hz, 1H), 4.41 (m, 2H), 3.51-3.40 (m, 4H), 2.98-2.89 (t, J=13 Hz, 1H), 2.28-2.25 (d, J=13.5 Hz, 1H), 1.83-1.74 (m, 3H).

Product 27a: (2Z,3E)-5'-chloro-3-((2-(piperazin-1-yl)ethoxy)imino)-[2,3'-biindolinylidene]-2'-one dihydrochloride (Compound 38, LDD-3555)

$^1$H NMR (400 MHz, DMSO-d$_6$) δ 11.83 (s, 1H), 10.84 (s, 1H), 8.60 (s, 1H), 8.24 (d, J=7.6 Hz, 1H), 7.45 (m, 2H), 7.14 (m, 2H), 6.88 (d, J=7.9 Hz, 1H), 4.69 (t, J=6.0 Hz, 2H), 3.46 (m, 4H), 2.84 (t, J=6.1 Hz, 2H), 2.69 (t, J=4.7 Hz, 2H), 2.45 (m, 2H).

Product 27b: (2Z,3E)-5'-chloro-3-((2-(4-methylpiperazin-1-yl)ethoxy)imino)-[2,3'-biindolinylidene]-2'-one dihydrochloride (Compound 39, LDD-3556)

$^1$H NMR (400 MHz, DMSO-d$_6$) δ 11.85 (s, 1H), 10.82 (s, 1H), 8.59 (s, 1H), 8.19 (d, J=7.6 Hz, 1H), 7.65 (m, 2H), 7.14 (m, 2H), 6.90 (d, J=7.9 Hz, 1H), 4.74 (m, 2H), 2.91 (m, 2H), 2.40 (m, 3H), 2.15 (m, 3H).

Product 28a: (2Z,3E)-5'-bromo-3-((2-(piperazin-1-yl)ethoxy)imino)-[2,3'-biindolinylidene]-2'-one dihydrochloride (Compound 40, LDD-3557)

$^1$H NMR (400 MHz, DMSO-d$_6$) δ 11.82 (s, 1H), 10.76 (s, 1H), 8.65 (s, 1H), 8.19 (d, J=8.0 Hz, 1H), 7.45 (m, 2H), 7.28 (d, J=8.2 Hz, 1H), 7.08 (m, 1H), 6.88 (d, J=8.0 Hz, 1H) 4.72 (m, 3H), 2.87 (m, 2H), 2.70 (m, 4H), 2.47 (m, 3H).

Product 28b: (2Z,3E)-5'-bromo-3-((2-(4-methylpiperazin-1-yl)ethoximino)-[2,3'-biindolinylidene]-2'-one dihydrochloride (Compound 41, LDD-3558)

$^1$H NMR (400 MHz, DMSO-d$_6$) δ 11.82 (s, 1H), 10.77 (s, 1H), 8.65 (s, 1H), 8.19 (d, J=8.0 Hz, 1H), 7.45 (m, 2H), 7.28 (d, J=8.2 Hz, 1H), 7.08 (m, 1H), 6.88 (d, J=8.0 Hz, 1H), 4.74 (m, 3H), 2.93 (m, 2H), 2.75 (m, 4H), 2.45 (m, 3H), 2.17 (m, 3H).

Product 29a: (2Z,3E)-5'-iodo-3-((2-(piperazin-1-yl)ethoxy)imino)-[2,3'-biindolinylidene]-2'-one dihydrochloride (Compound 42, LDD-3559)

$^1$H NMR (400 MHz, DMSO-d$_6$) δ 11.83 (s, 1H), 10.80 (s, 1H), 8.85 (s, 1H), 8.20 (d, J=8.0 Hz, 1H), 7.45 (m, 3H), 7.06 (m, 1H), 6.75 (d, J=8.0 Hz, 1H) 4.75 (m, 3H), 2.85 (m, 2H), 2.71 (m, 4H), 2.45 (m, 3H).

Product 29b: (2Z,3E)-5'-iodo-3-((2-(4-methylpiperazin-1-yl)ethoxy)imino)-[2,3'-biindolinylidene]-2'-one dihydrochloride (Compound 43, LDD-3560)

$^1$H NMR (400 MHz, DMSO-$d_6$) δ 11.82 (s, 1H), 10.77 (s, 1H), 8.66 (s, 1H), 8.21 (d, J=8.0 Hz, 1H), 7.46 (m, 3H), 7.08 (m, 1H), 6.74 (d, J=8.0 Hz, 1H), 4.75 (m, 3H), 2.90 (m, 2H), 2.72 (m, 4H), 2.42 (m, 3H), 2.17 (m, 3H).

Product 30a: (2Z,3E)-34(2-(piperazin-1-yl)ethoxy)imino)-5'-(trifluoromethoxy)-[2,3'-biindolinylidene]-2'-one dihydrochloride (Compound 44, LDD-3561)

$^1$H NMR (400 MHz, D$_2$O) δ 7.53 (m, 2H), 7.03-7.00 (t, J=7.2 Hz, 1H), 6.76-6.72 (t, J=7.2 Hz, 1H), 6.60-6.58 (d, J=8.4 Hz, 1H), 6.38-6.36 (d, J=7.6 Hz, 1H), 6.26-6.24 (d, J=8.4 Hz, 1H), 4.34 (brs, 2H), 3.74-3.55 (m, 10H).

Product 30b: (2Z,3E)-3-((2-(4-methylpiperazin-1-yl)ethoxy)imino)-5'-(trifluoromethox[2,3'-biindolinylidene]-2'-one dihydrochloride (Compound 45, LDD-3562)

$^1$H NMR (400 MHz, DMSO-$d_6$) δ 11.75 (s, 1H), 10.99 (s, 1H), 9.62 (m, 2H), 8.50 (s, 1H), 8.24 (d, J=7.80, 1H), 7.44-7.41 (m, 2H), 7.13-7.10 (m, 1H), 7.43-7.00 (m, 1H), 6.94 (d, J=8.28 Hz, 1H), 4.92 (m, 2H), 3.59-3.37 (m, 13H, overlapped in solvent peak).

Product 31a: (2Z,3E)-5'-methoxy-3-((2-(piperazin-1-yl)ethoxy)imino)-[2,3'-biindolinylidene]-2'-one dihydrochloride (Compound 46, LDD-3563)

$^1$H NMR (400 MHz, DMSO-$d_6$) δ 11.73 (s, 1H), 10.61 (s, 1H), 8.25 (d, J=7.32 Hz, 1H), 8.20 (m, 1H), 7.43-7.37 (m, 2H), 6.98 (t, J=6.36 Hz, 1H), 6.78 (d, J=8.80 Hz, 1H), 6.73 (dd, J=8.28, 2.44 Hz, 1H), 4.80 (m, 2H), 3.60-3.37 (m, 10H), 2.77 (s, 3H).

Product 31b: (2Z,3E)-5'-methoxy-3-((2-(4-methylpiperazin-1-yl)ethoxy)imino)-[2,3'-biindolinylidene]-2'-one dihydrochloride (Compound 47, LDD-3564)

$^1$H NMR (400 MHz, DMSO-$d_6$) δ 11.72 (s, 1H), 10.61 (s, 1H), 9.69 (m, 2H), 8.24 (d, J=7.32 Hz, 1H), 8.19 (d, J=2.92 Hz, 1H), 7.44-7.36 (m, 2H), 6.99 (t, J=7.32 Hz, 1H), 6.79-6.77 (d, J=8.76 Hz, 1H), 6.74-6.71 (dd, J=8.80, 2.92 Hz, 1H), 4.98 (m, 2H), 3.76-3.55 (m, 13H, partially overlapped with water).

The thus-obtained compounds were dissolved in DMSO (Fisher, Waltham, Mass., USA) at a concentration of 10 mmol/L and stored at −20° C.

Example 2

Anti-Tumor Activity

Experimental Method
2-1. Cell Culture

MV4; 11 human acute myeloid leukemia cells were purchased from the American Type Culture Collection (ATCC, Rockville, Md., USA, CRL-9591), and the cells were cultured in IMDM medium (Sigma Co., St. Louis, Mo., USA) supplemented with 10% fetal bovine serum, 1% penicillin/streptomycin, and 4 mM L-glutamine (Life Technology, Grand Island, N.Y.). MDA-MB-231 (metastatic breast cancer, ATCC HTB-26), Jurkat (human acute T lymphocytic leukemia, ATCC TIB-152), and K-562 (human chronic myelogenous leukemia, ATCC CCL-243) cells were cultured in RPMI-1640 (Sigma Co.). MCF7 (human breast adenocarcinoma, ATCC HTB-22) and PC-3 (human prostate adenocarcinoma, ATCC CRL-1435) cells were cultured in DMEM (Sigma Co.) medium supplemented with 10% fetal bovine serum and 1% penicillin/streptomycin. The cultured cells were incubated at 3° C. with 5% CO$_2$.

Cell viability was assessed by a tetrazolium-based assay using the EZ-Cytox Cell Viability Assay kit (DaeilLab, Korea). Briefly, 2,000 to 15,000 cells were plated in 96-well plates in 100 μl of medium. The next day, the cells were treated with compounds together with dimethyl sulfoxide (DMSO) as a negative control. Three days (72 hours) after the drug addition, 15 μl of the EZ-Cytox kit reagent was added to each well of the 96-well plate and then incubated at 37° C. in a humidified CO$_2$ incubator for 4 hours. After incubation, the optical density (OD) was measured at a wavelength of 450 nm using a Victor multilabel reader (Perkin Elmer, Waltham, Mass., USA). The IC$_{50}$ was calculated by nonlinear regression using Prism version 5.01 (GraphPad, La Jolla, Calif., USA).

2-2. In Vitro Kinase Analysis

Inhibition of the FLT3 kinase activity was measured using homogeneous, time-resolved fluorescence (HTRF) assays. Recombinant proteins containing the FLT3 kinase domain were purchased from Carna biosciences (Japan). Optimal enzyme, ATP, and substrate concentrations were established using the HTRF KinEASE kit (Cisbio, France) according to the manufacturer's instructions. The FLT3 enzymes were mixed in sequence with diluted compounds and peptide substrates in a kinase reaction buffer (50 mM HEPES (pH 7.0), 500 μM ATP, 0.1 mM sodium orthovanadate, 5 mM MgCl$_2$, 1 mM DTT, 0.01% bovine serum albumin (BSA), and 0.02% NaN$_3$). After the addition of the reagents for detection, the TR-FRET signal was measured using a Victor multilabel reader (Perkin Elmer, Waltham, Mass., USA). The IC$_{50}$ was calculated by nonlinear regression using Prism version 5.01 (GraphPad). JAK2, JAK3, cMET, and RET in vitro kinase assays were also performed using the HTRF assay.

In vitro kinase analysis for IRAK4 was performed using the LANCE Ultra Kinase Activity Assay (Perkin Elmer) including ULight-p70S6K (Thr389) peptide (phosphorylation motif FLGFTYVAP). The assays consisted of enzymes mixed with sequentially diluted compounds, 50 nM ULight-p70S6K (Thr389) peptide, and 500 μM ATP, which were pre-diluted in kinase buffer (50 mM HEPES (pH 7.5), 10 mM MgCl$_2$, 1 mM EGTA, 2 mM DTT and 0.01% Tween20). The kinase reaction was incubated at 25° C. for 90 minutes and terminated by adding 10 mM EDTA. For the detection of phospho-substrate, the Eu-anti-phospho-p70S6K (Thr389) antibody diluted with detection buffer was added to a final concentration of 2 nM, and the reacted products were incubated at 25° C. for 1 hour. The signal was measured with an EnVision multi-label reader.

2-3. Mouse Tumor Xenograft (Xenograft MV4;11)

MV4; 11 cells were inoculated subcutaneously in the flank of female BALB/c nu/nu (athymic nude) mice ($5\times10^6$ cells/mouse). When the tumor reached an average volume of 100 mm$^3$ (approximately 14 days after inoculation), the mice were randomly divided into 3 groups (n=10 for control group, n=6 for 5 mg/kg or 10 mg/kg groups) and injected with 5 mg/kg or 10 mg/kg of LDD1937 at 20 ml/kg in PBS, or pure PBS (control) in the tail vein. The drug or the control PBS was injected daily for a duration of 21 days. The tumor size was measured twice a week for 21 days, and the tumor volume was calculated with the following equation: V (volume)=X (length)×D (width)$^2$/2. After 21 days, the mice were sacrificed, and tumor weights were measured.

2-4. Mouse Tumor Xenograft (Xenograft MDA-MB-231)

6-weeks-old Balb/c nu/nu mice (female) were purchased from Central Lab. Animal Inc. to be used. The MDA-MB-231 cell line was purchased from ATCC to be used. $1\times10^7$ of cells were inoculated for each mouse in order to make a tumor bearing mice model, and 100 uL of a corning matrigel/PBS mix solution was used as a solvent. The administration of the drug was initiated when the tumor volume reached 200 mm$^3$ to 300 mm$^3$ (in principle, the tumor volume was measured daily, and the volume was calculated by the following equation: V (volume)=X (length)×D (width)$^2$/2).

The candidate substances LDD-2614 (Compound 21), 2633 (Compound 28), 2634 (Compound 34), 2635 (Compound 33) were administered at 20 mg/kg/p.o/day, and doxorubicin, which was a control, was administered at 5 mg/kg/i.p (once a week) for 4 weeks.

Experimental Results 2-5. LDD1937 as Inhibitor of FLT3 Kinase Activity

Table 1 shows the inhibitory activity against FLT3 and MV4;11.

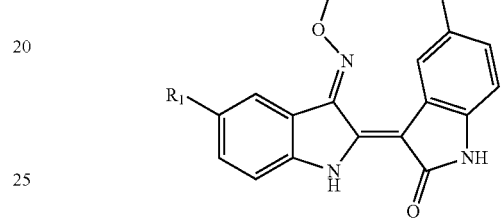

TABLE 1

| Cmpd | $R_1$ | $R_2$ | $R_3$ | IC$_{50}$ (nM) FLT3$^a$ | MV4$_{a;11}^a$ |
|---|---|---|---|---|---|
| 1 LDD-1075 | H | COOCH$_3$ | H | 2890 | 41 |
| 2 LDD-1916 | H | COOCH$_3$ | CH$_2$CH$_2$Br | 19 | 51 |
| 3 LDD-1918 | H | COOCH$_3$ | CH$_2$CH$_2$NH$_2$•HCl | 5 | 15 |
| 4 (LDD1937) | H | COOCH$_3$ | CH$_2$CH$_2$N(piperazine)NH •2HCl | 3 | 1 |
| 5 LDD-1938 | H | COOCH$_3$ | CH$_2$CH$_2$N(piperazine)N— •2HCl | 11 | 11 |
| 6 LDD-1943 | H | COOCH$_3$ | CH$_2$CH$_2$N(morpholine)O •HCl | 253 | 53 |
| 7 LDD-1076 | H | COOCH | H | 8 | 4020 |
| 8 LDD-1939 | H | COOCH | CH$_2$CH$_2$Br | 13 | 340 |
| 9 LDD-1936 | H | COOCH | CH$_2$CH$_2$NH$_2$•HCl | 3 | 150 |
| 10 (LDD1940) | H | COOCH | CH$_2$CH$_2$N(piperazine)NH •2HCl | 3 | 40 |
| 11 LDD-1941 | H | COOCH | CH$_2$CH$_2$N(piperazine)N— •2HCl | 3 | 176 |
| 12 LDD-1944 | H | COOCH | CH$_2$CH$_2$N(morpholine)O •HCl | 8 | 1000 |
| CEP-701 | | | | 3 | 33 |

Table 2 shows the inhibitory activity of Compounds 13 to 37 against FLT3, MV4;11, and MDA-MB-231.
TABLE 2
| Compound | R₁ | R₂ | R₃ | IC$_{50}$(nM) FLT3[a] | GI$_{50}$(nM) MV4;11 | GI$_{50}$(nM) MDA-MB-231 |
|---|---|---|---|---|---|---|
| 13 (LDD-963) | OH | NO$_2$ | H | 23.4 | 170 | 567.6 |
| 14 (LDD-1893) | OH | NO$_2$ | 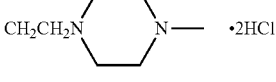 | 18.9 | 50 | 29.10 |
| 15 (LDD-2365) | H | NO$_2$ | CH$_2$CH$_2$NH$_2$·HCl | N.A | N.A | >1 |
| 16 (LDD-2366) | H | NO$_2$ | 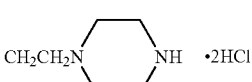 | 13.2 | 7.01 | 74.30 |
| 17 (LDD-2612) | F | NO$_2$ | 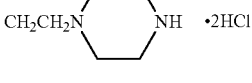 | 35.5 | 10.2 | 88.80 |
| 18 (LDD-2613) | F | NO$_2$ | 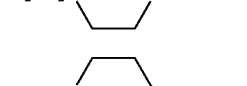 | 35.5 | 118.1 | 69.70 |
| 19 (LDD-2835) | F | NO$_2$ |  | 453 | 1.49 | 804.10 |
| 20 (LDD-2836) | F | NO$_2$ | 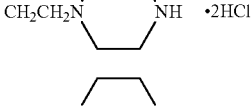 | 112 | 446.7 | 144.1 |
| 21 (LDD-2614) | F | F | 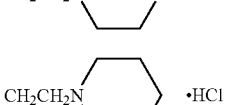 | 26.2 | 8.9 | 120.6 |
| 22 (LDD-2615) | F | F | 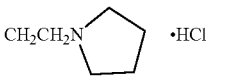 | 40.4 | N.A | 600.4 |
| 23 (LDD-2766) | F | F | 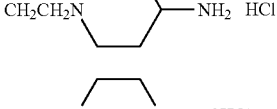 | 45 | 3.19 | >1 |
| 24 (LDD-2770) | F | F | 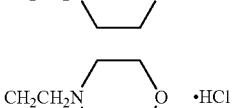 | 116 | 633.9 | 346.90 |
| 25 (LDD-2853) | F | F | 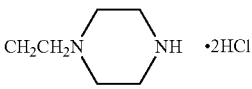 | 81.5 | 85.67 | >1 |
| 26 (LDD-2767) | F | F |  | 45.2 | 8.47 | 972.2 |
| 27 (LDD-2834) | F | F |  | 939 | 115.5 | >10 |
| 28 (LDD-2633) | H | H |  | 2.7 | 0.51 | 275.5 |

TABLE 2-continued
| Compound | R₁ | R₂ | R₃ | IC₅₀(nM) FLT3[a] | GI₅₀(nM) MV4;11 | GI₅₀(nM) MDA-MB-231 |
|---|---|---|---|---|---|---|
| 29 (LDD-2632) | H | H | 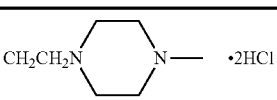 | 7.42 | 54.8 | 483.4 |
| 30 (LDD-2870) | H | H | 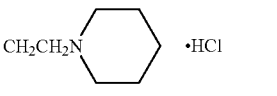 | 251 | 138.5 | >1 |
| 31 (LDD-2872) | H | H |  | 51.9 | 103.5 | 313.10 |
| 32 (LDD-2871) | H | H | 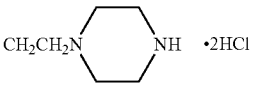 | 50.9 | 15.1 | 320.30 |
| 33 (LDD-2635) | H | F | 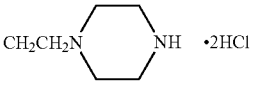 | 0.9 | 1.0 | 116.6 |
| 34 (LDD-2634) | H | F | 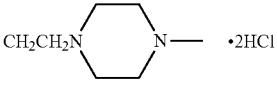 | 3.2 | 11.09 | 126.6 |
| 35 (LDD-2768) | H | F | 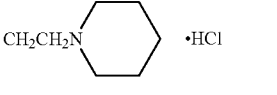 | 142 | 263.3 | 804.8 |
| 36 (LDD-2771) | H | F | 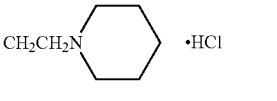 | 267 | 212 | 805 |
| 37 (LDD-2769) | H | F | 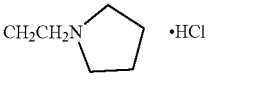 | 9.47 | 11.9 | 362.12 |
| 38 (LDD-3555) | H | Cl | 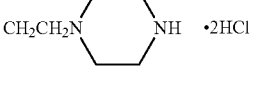 | 1.3 | 11.0 | — |
| 39 (LDD-3556) | H | Cl | 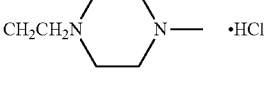 | 2.4 | 37.0 | — |
| 40 (LDD-3557) | H | Br | 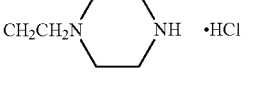 | 1.0 | 10.0 | — |
| 41 (LDD-3558) | H | Br | 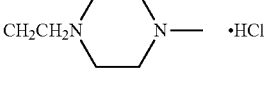 | 4.8 | 25.0 | — |
| 42 (LDD-3559) | H | I | 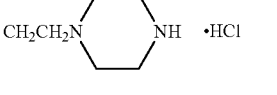 | 1.8 | 9.0 | — |
| 43 (MD-3560) | H | I | 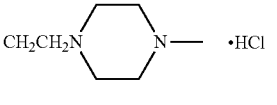 | 5.8 | 32.0 | — |
| 44 (LDD-3561) | H | OCF₃ | 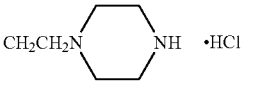 | 40.2 | 20.0 | — |

TABLE 2-continued

| Compound | R₁ | R₂ | R₃ | IC₅₀(nM) FLT3$^a$ | GI₅₀(nM) MV4;11 | GI₅₀(nM) MDA-MB-231 |
|---|---|---|---|---|---|---|
| 45 (LDD-3562) | H | OCF₃ | CH₂CH₂N(piperazine)N—·HCl | 5.6 | 22.0 | — |
| 46 (LDD-3563) | H | OCH₃ | CH₂CH₂N(piperazine)NH·HCl | 12.4 | 17.0 | — |
| 47 (LDD-3564) | H | OCH₃ | CH₂CH₂N(piperazine)N—·HCl | 2.1 | 7.0 | — |

The activity of each compound was tested for 3 times.

The present inventors have previously reported that a series of 5-substituted indirubin derivatives are as potent FLT3 inhibitors, which effectively inhibit the growth of acute myeloid leukemia cells [21]. Although indirubin had a potent kinase inhibitory effect, its poor solubility in water caused some physiological problems. In order to address the solubility problems of these indirubin derivatives, the present inventors have designed and synthesized novel analogues having hydrophilic functional groups on the molecules.

Recently, the present inventors have found that the 5-carboxy indirubin derivative 7 strongly inhibited FLT3 kinase ($IC_{50}$=8 nM) lacking anti-proliferative activity against the human leukemia cell line MV4; 11, which expresses FLT3-ITD (see Table 1). Interestingly, the corresponding 5-carboxy ester analogue 1 showed potent anti-proliferative activity against MV4; 11 cells ($IC_{50}$=41 nM) despite of very weak FLT3 inhibitory activity. Therefore, the present inventors have attempted optimization to increase the growth inhibitory activity of FLT3 kinase and MV4; 11 by performing further derivatization at the 3' position of the indirubin backbone.

It has been reported that 3'-alkyl substitution of indirubin oxime derivatives for other kinases confers advantages such as higher potency and water solubility. While there have been no reports on 3'-alkyl substituted indirubin oxime derivatives having 5-carboxylic acid or ester groups as FLT3 inhibitors, the present inventors synthesized these analogues so as to obtain the advantage of the alkyl substitution at the 3' oxime position. The inhibitory effect of the 3'-substituted indirubin analogues is described in Table 1. In general, the alkyl substituted compounds showed an increased inhibitory activity against both FLT3 and MV4; 11 compared to Compounds 1 and 7. The analogues of 5-ester substituted Compound 1 showed a potent inhibitory activity against FLT3 kinase as well as MV4; 11 cells. However, the 5-carboxy derivatives (9-12) showed an inhibitory activity slightly lower than that of the 5-ester analogues (3-6) despite of a strong inhibitory activity against FLT3 kinase. The inhibitory effects against FLT3 and MV4; 11 depended on the substituent at the R position. The inhibitory activity against FLT3 increased in the order of morpholine, ethyl bromide<N-methyl piperazine<amine, piperazine, while the inhibitory activity against MV4; 11 increased in the following order: morpholine, ethyl bromide<amine, N-methyl piperazine<piperazine. The ethyl bromide and morpholine substitutions at the R position (Compounds 2, 6, 8 and 12) did not have a crucial effect on the inhibitory ability against FLT3 and MV4; 11. The ethyl piperazine Compounds 4 and 10 showed the most potent inhibitory activity against FLT3 ($IC_{50}$=3 nM) and MV4; 11 ($IC_{50}$=1 nM and 40 nM) in each series. Moreover, Compound 4 more potently inhibited the growth of MV4; 11 cells than CEP-701, a well-known FLT3 inhibitor. Surprisingly, all alkyl-substituted series of 5-methyl ester Compound 1 showed a significantly increased inhibitory activity against FLT3 kinase. The ethyl piperazine-substituted Compound 4 showed the most potent activity against both FLT3 ($IC_{50}$=3 nM) and MV4; 11 ($IC_{50}$=1 nM), the activity of which was increased by 1000-fold and 40-fold, respectively, compared to the starting Compound 1. Additionally, the introduction of an alkyl substituent at the 3'-oxime position of 5-carboxylic acid indirubin 7 significantly improved the inhibitory effect against MV4; 11. Similar to the 5-methyl ester family, piperazine-substituted Compound 10 showed the most potent inhibitory effect against both FLT3 and MV4; 11. However, Compound 10 showed a moderate inhibitory activity only against MV4; 11 cells, despite its potent inhibitory activity against FLT3 kinase. The present inventors predicted that the 5-carboxylic acid derivatives would be too polar to pass through the cell membrane.

In the process of identifying the receptor tyrosine kinase inhibitors, several indirubin analogues were synthesized, and their structure activity relationship was investigated (Table 1). Among 12 compounds, Compound 4 (LDD1937, FIG. 1A), methyl (2Z,3E)-2'-oxo-3-((2-(piperazin-1-yl)ethoxy)imino)-[2,3'-biindolinylidene]-5'-carboxylate dihydrochloride was selected and further characterized. As shown in FIG. 1B, the $IC_{50}$ of Compound 4 (LDD1937) against the FLT3 kinase activity was 3 nM. The $IC_{50}$ values of Compound 4 against other kinase activities were also measured (Table 3). There was at least a 170-fold difference in the $IC_{50}$ between FLT3 and other kinases.

TABLE 3

| Kinase | $IC_{50}$ (μM) |
|---|---|
| FLT3 | 0.003 ± 0.00052 |
| JAK2 | 0.52 ± 0.0727 |
| JAK3 | 0.69 ± 0.0599 |
| cMET | 0.25 ± 0.074 |
| IRAK4 | 0.30 — |

Data indicate mean ± S.D.

2-6. Inhibition of MV4; 11 Cell Proliferation and Induction of Selective Apoptotic Cell Death of LDD1937

MV4, 11 cells are leukemia cells with a receptor tyrosine kinase FLT3 mutation. The MV4; 11 cells harbor a FLT3 mutation (FLT3-ITD) with an internal tandem duplication (ITD) in the juxtamembrane domain, which causes the constitutive activation of FLT3 activity [3]. MV4; 11 cell growth and survival are known to depend on the FLT3 activity [23]. The cytotoxicity by LDD1937 was measured and shown in Table 4. Immortalized T lymphocytes Jurkat cells, prostate cancer PC-3 cells, breast cancer MCF-7 cells, and erythropoiesis K562 cells were also used for the cytotoxicity assay. The MV4; 11 cells showed a high sensitivity to the LDD1937 treatment ($GI_{50}$=1 nM) compared to other cell lines. In terms of the $GI_{50}$ values, LDD1937 was 1000 to 2000 times more potent in the MV4; 11 cells than in other cell lines.

TABLE 4

| Cell line | $GI_{50}$ (µM) |
| --- | --- |
| MV-4-11 | 0.0012 ± 0.00015 |
| Jurkat | 1.44 ± 0.29 |
| PC-3 | 1.1 ± 0.14 |
| MCF-7 | 2.14 ± 0.16 |
| K562 | 1.21 ± 0.33 |

Data indicate mean ± S.D.

2-7. In Vivo Tumor Growth Inhibition of LDD1937

In order to examine the efficacy of LDD1937 in vivo, an MV4; 11 xenograft study was performed. MV4; 11 cells were injected subcutaneously into BALB/c nu/nu mice to grow tumors to a size of approximately 100 mm³. Additionally, LDD1937 or the PBS control was administered intravenously for 3 weeks. As shown in FIG. 2A, the tumor size of the LDD1937 group was significantly smaller than those of the control group. In particular, in the 10 mg/kg group, the tumor disappeared from day 3, which was based on the measured tumor volume (FIG. 2A). Dissection of the tumor injection site confirmed the complete disappearance of the tumor mass in the 10 mg/kg group. Therefore, the tumor weight could only be measured in the control group and the 5 mg/kg group, and there was a significant decrease in the tumor weight in the 5 mg/kg group of the LDD1937 (FIG. 2B). Further, there was no significant difference in body weight between the groups during the administration period (FIG. 3).

2-8. In Vivo Anticancer Effect of 4 Compounds

In order to examine the in vivo efficacy of four indirubin derivatives, an MDA-MB-231 xenograft study was performed. The cultured cells were grown in BALB/c nu/nu (female) mice to a tumor size of approximately 200 mm³ to 300 mm³. Additionally, four indirubin derivatives, LDD-2614 (Compound 21), 2633 (Compound 28), 2634 (Compound 34), and 2635 (Compound 33) were each administered at 20 mg/kg. As a Comparative group, doxonibicin was administered at 5 mg/kg for 4 weeks. As shown in FIG. 4, there was no significant difference in the weights of the liver and the kidney after administration of the four compounds, but there was some difference in the weight of cancer tissue. During the same period, it was confirmed that the volume of cancer tissue was reduced to a level similar to those of the control group (FIG. 5). The dissection of the tumor injection site confirmed that three compounds of 2633 (Compound 28), 2634 (Compound 34), and 2635 (Compound 33) showed anticancer effects similar to the Comparative Group (FIG. 6)

FMS-like receptor tyrosine kinase-3 (FLT3) belongs to the family of receptor tyrosine kinase (RTK), and FLT3 mutations were observed in ⅓ of patients with acute myeloid leukemia (AML). As described above, the present inventors have identified a potent FLT3 inhibitor LDD1937, which includes an indirubin skeleton. The potent inhibitory activity of LDD1937 against FLT3 was shown with an in vitro kinase assay (($IC_{50}$=3 nM). The LDD1937 compound selectively inhibited the growth of MV4;11 cells ($GI_{50}$=1 nM)) and induced apoptotic cell death. LDD1937 caused cell cycle arrest at the $G_2$/M phase and increased the cell population at the sub-$G_1$ phase. Phosphorylation of STATS, a downstream signaling of FLT3, was significantly reduced by LDD1937 in a dose-dependent manner. The pharmacokinetic properties of LDD1937 were investigated in mice. Additionally, the in vivo anti-tumor effect was assessed using MV4; 11 xenografts. The tumor volume and weight were significantly decreased compared to the control group with the intravenous administration of 5 mg/kg and 10 mg/kg in nu/nu mice.

Example 3

Anti-Tumor Activity

Experimental Method 3-1. FLT3-ITD Binding Affinity Assay

FLT3-ITD binding affinity assays were performed using the LanthaScreen Assay according to the manufacturer's instructions (Thermo Fisher Scientific). FLT3 ITD is supplied at a concentration printed on the product label. The molecular weight of the kinase is 78.6 kDa, which can be found on the kinase Certificate of Analysis shipped with the product. The kinase molecular weight will be needed to convert the concentration to molarity as required in the following protocol. Kinase Buffer A is supplied as a 5× concentrated stock. Prepare a 1× solution by adding 4 mL of the 5× solution to 16 mL of distilled $H_2O$. The 1× kinase reaction buffer is stable at room temperature. 1× Kinase Buffer A consists of 50 mM HEPES pH 7.5, 10 mM $MgCl_2$, 1 mM EGTA, 0.01% Brij-35. Kinase Tracer 236 is prepared as a 50 µM stock in DMSO. Add 4 µL of each concentration of serially diluted compound to triplicate assay wells in a 384-well plate. Add 8 µL of kinase/antibody solution and 4 µL of tracer solution to all wells. Incubate the plate at room temperature for 60 min and read using Perkin Elmer (EnVision®, Victor, and ViewLux).

3-2. FLT3-D835Y Inhibitory Activity

Recombinant protein kinase assays were performed using the FRET-based Z'-LYTE Kinase Assay according to the manufacturer's instructions (Thermo Fisher Scientific). Recombinant FLT3-D835Y kinase domain proteins were purchased from Life Technologies, while recombinant Fes was expressed in E. coli and purified. Kinases were preincubated with inhibitors for 30 minutes, followed by addition of ATP and substrate for 1 hour. Reactions were quenched by addition of development reagent, followed by incubation for an additional hour prior to fluorescence measurements on a SpectraMax M5 microplate reader. $IC_{50}$ values were calculated by non-linear regression analysis of the resulting concentration-response curves using GraphPad PRISM.

3-3. In Vitro FLT3 Kinase Assay

The inhibition of the FLT3 kinase activity was measured with homogeneous, time-resolved fluorescence (HTRF) assays. Recombinant proteins containing the FLT3 kinase domain were purchased from Invitrogen (Carlsbad, Calif., USA). Optimal enzyme, ATP, and substrate concentrations were established with the HTRF KinEASE kit (Cisbio, France) according to the manufacturer's instructions. The FLT3 enzymes were mixed with serially diluted compounds and peptide substrates in a kinase reaction buffer (50 mM HEPES (pH 7.0), 500 μM ATP, 0.1 mM sodium orthovanadate, 5 mM $MgCl_2$, 1 mM DTT, 0.01% bovine serum albumin (BSA), and 0.02% $NaN_3$). Ten microliters of the total volume of the kinase reaction were added to the wells of a 96-well assay plate. The kinase reactions were incubated for 30 min at 25° C. For the detection of the phospho-substrate, the Eu3b-Cryptate-conjugated mouse monoclonal antibody (PT66) and the streptavidin-XL665 (SA-XL) were added, and the reactions were then incubated for 1 hour at 25° C. The signal was measured on an Victor X5 multi-label reader (PerkinElmer, Waltham, Mass., USA). The curve was fitted by nonlinear regression, and the $IC_{50}$ was calculated using GraphPad Prism 5.01 (GraphPad, La Jolla, Calif., USA).

3-4. Cell Culture

MV4-11 human acute myeloid leukemia cells were purchased from the American Type culture collection (ATCC). The cells were maintained in DMEM medium (Sigma Co., St. Louis, Mo., USA) with 10% Fetal bovine serum and 1% pencillin/streptomycin in a humidified incubator at 37° C. with 5% $CO_2$. K562 chronic myeloid leukemia cells were purchased from the ATCC. The cells were maintained in DMEM medium (Hyclone) with 10% Fetal bovine serum (Gibco) and 1% penicillin/streptomycin. MOLM14 were purchased from the ATCC and the cells were maintained in RPMI medium (Hyclone) with 10% Fetal bovine serum (Gibco) and 1% penicillin/streptomycin.

3-5. Cytotoxicity Assay Protocol of MV4-11 Cells 10,000 Cells were plated in 96-well plates in 100 μL fresh medium (DMEM containing 10% FBS) and serial dilutions of compounds were added. Test 96-well plates were incubated at 37° C. with 5% $CO_2$ for 72 h. After 72 h incubation, 10 μL of the EZ-Cytox kit reagent from EZ-cytox Cell viability assay kit (DaeilLab, Korea) were added to each well of the 96-well plate and then incubated at 37° C. with 5% $CO_2$ for 3 h. After 3h incubation, metabolically active cells were measured spectrophotometrically at a wavelength of 450 nm with a Victor multilabel reader (Perkin Elmer, Waltham, Mass., USA). The $IC_{50}$ values were calculated with nonlinear regression analysis using OriginPro 9.1 software (OriginLab, Northampton, Mass.).

3-6. Site-Directed Mutagenesis and Viral Infection

Mutagenesis is performed in FLT3-ITD MSCV plasmid using Q5 site-directed mutagenesis kit (E05545). D835Y, F691L mutations were introduced into FLT3-ITD plasmid according to the manufacturer's protocol. HEK293T cells were transfected with plasmid DNA using Polyplus Reagent (114-07) according to manufacturer's instructions. Experiments were performed 24-48 hr after transfection. Retroviral particles were produced by transiently transfecting HEK293T cells with Retroviral vectors together with packaging vectors, GPE and VSVG. 48 h after transfection, media containing viral particles were collected and filtered for infection. Viral particles were infected to MOLM14 cells and 48 h after infection, infected cells were selected with puromycin (1 μg/mL).

3-7. Cell Proliferation Assay

Cell proliferation was assessed by MTT assay against various MOLM14 cells according to the manufacturer's recommendations (11465007001, Roche)

3-8. Mouse Tumor Xenograft

MV-4-11 cells were inoculated subcutaneously in the flank of female BALB/c nu/nu (athymic nude) mice ($5\times10^6$ cells per mouse). When the tumor reached a mean volume of 100 mm3 (approximately 14 days after inoculation), the mice were randomly divided into three groups (n=10 for the control group and n=6 for the compound 36 and 41 test groups) and 10 ml/kg of compound 36, 41 in PBS, or pure PBS (control) were orally administered. The drug or the control PBS was administered daily for a duration of 21 days. Tumor sizes were measured twice a week for 21 days, and the tumor volumes were calculated with the following formula: V (volume)=X (length)×D (width)2/2. After 21 days, the mice were sacrificed, and the tumor weights were measured. All experiments were approved by the Institutional Animal Care and Use Committee of Korea Institute of Toxicology (KIT) and conducted according to the guidelines of Association for Assessment and Accreditation of Laboratory Animal Care International.

Experimental Results 3-9. The Structure of Compound 33 (LDD-2635) and In-Vitro Kinase Activity for FLT3 and FLT3/D835Y Mutant To investigate kinase biological activities against FLT3 wild type and mutant kinases, we screened a single concentration of 100 nM of Compound 33 (LDD-2635) (FIG. 7). Remarkably, the inhibition of the mutant FLT3/D835Y (0.32 nM) turned out to be more potent than that of the wild type FLT3 ($IC_{50}$=0.87 nM). Moreover, Compound 33 (LDD-2635) displayed strong binding affinity at FLT3-ITD with a Kd value of <0.25 nM (Table 5).

3-10. Anti-Cancer Activity of Compound 33 (LDD-2635) at AML Cell Lines Including FLT3 Mutant Expressing MOLM14

Since the FLT3 and FLT3(D835Y) inhibitory activities and the binding affinity for FLT3-ITD of Compound 33 (LDD-2635) were detellnined as sub-nanomolar range of $IC_{50}$ and Kd values (0.87 nM 0.32 nM and <0.25 nM, respectively), the anti-proliferative activities of Compound 33 (LDD-2635) were assessed against several FLT3-ITD positive human AML cell line including MOLM14 wild type, other clinically relevant mutant kinase expressed MOLM14 FLT3-ITD (MOLM14-ITD), MOLM14 FLT3-ITD-D835Y (MOLM14-ITD-D835Y) and MOLM14 FLT3-ITD-F691L (MOLM14-ITD-F691L) cells that are FLT3 growth dependent (Table 5). $GI_{50}$ value of Compound 33 (LDD-2635) and other anti-cancer reagents against tested cell lines. All data ware obtained by triplet testing.

TABLE 5

Anti-proliferative activities of compound 36 against MOLM14 mutant cells.

| | $GI_{50}$ (nM) | | | |
|---|---|---|---|---|
| Compound | MOLM14 Wild type | MOLM14-ITD | MOLM14-ITD D835Y | MOLM14-ITD F691L |
| LDD-2635 | 4.88 | 1.85 | 1.87 | 3.27 |
| Quizartinib | 17 | — | 54 | 26 |
| Crenolanib | 4.7 | — | 15 | 20 |
| Gilteritinib | 8.5 | — | 43 | 24 |
| Midostaurin | 80 | — | 79 | 37 |
| Sorafenib | 28 | — | No Activity | No Activity |

In the same experiments, positive control drugs were also tested in parallel. As the results, Compound 33 (LDD-2635) showed similar dose-dependent anti-proliferative activity against MOLM14 wild type cell line with a $GI_{50}$ values of 4.88 nM compared to Gilteritinib ($GI_{50}$=8.5 nM). In addition, Compound 33 (LDD-2635) was more sensitive to MOLM14-ITD cells ($GI_{50}$=1.85 nM) than MOLM14 wild type. In the evaluation of the anti-proliferative effects against MOLM14-ITD and ITD-TKD dual mutant cell lines, MOLM14(FLT3-ITD, D835Y and F691L), Compound 33 (LDD-2635) retained potent anti-proliferative effects against MOLM14 (FLT3-ITD-D835Y and FLT3-ITD-F691L) mutant cells ($GI_{50}$=1.87 and 3.27 nM, respectively) whereas other drugs including Quizartinib, Crenolanib, Gilteritinib, Midostaurin and Sorafenib showed much lower inhibitory activities as shown in Table 5.

3-11. Selectivity Profiles of Compound 33 (LDD-2635) in Various Human Cancer Cell Lines To evaluate the selective anti-proliferative activities of the representative Compound 33 (LDD-2635) in the FLT3-ITD expressing AML cells, MV4-11, we examined WST assay to measure the cytotoxicity of Compound 33 (LDD-2635) against several other cancer cell lines, including chronic myeloid leukemia (K562), lung cancer (A549), liver cancer (HepG2), triple negative breast cancer (MDA-MB-231), colon cancer (HCT-116), prostate cancer (PC3) and ovarian cancer (SK-OV-3). (Table 6)

Compound 33 (LDD-2635) was tested at 8 concentrations to measure their anti-proliferative effects on various human cancer cell lines using WST assay. The $GI_{50}$ values were obtained in triplicate and the error bars represent the standard error of the mean.

TABLE 6

Anti-proliferative Activities of LDD-2635 against Various Cancer Cell Lines

| Cell line | $GI_{50}$ value (μM) or % inhibition at 1 μM$^a$ of Comp. 36 (LDD-2635) |
|---|---|
| MV4-11 | 0.001 ± 0.0003 |
| A549 | 2.05% |
| HepG2 | 1.1 ± 0.2 |
| HCT-116 | 38.46% |
| PC3 | 40.67% |
| SK-OV-3 | 16.04% |

As the results, Compound 33 (LDD-2635) showed 430 times more sensitive against MV4-11 cells ($GI_{50}$=1 nM) than K562 cell line, which is insensitive to FLT3 inhibitors. Furthermore, Compound 33 (LDD-2635) displayed excellent selectivity profiles against other cancer cell lines.

3-12. In vivo Anti-tumor Activity of LDD-2635 and LDD-2633

An in vivo MV4-11 xenograft study was performed to determine the efficacy of the indirubin derivatives. MV4-11 cells were subcutaneously injected into BALB/c nu/nu mice, and tumors were allowed to grow to a size of approximately 100 mm³. Compound 33 (LDD-2635) and Compound 28 (LDD-2633) were selected for in vivo testing because of their significant FLT3 inhibitory activity and MV4-11 anti-proliferative activity. A single oral dose of 20 mg/kg of Compound 33 (LDD-2635), Compound 28 (LDD-2633) or the PBS control was administered once daily for 21 days.

As shown in FIG. 8A, we found that treatment with both compounds resulted in the rapid and complete remission of tumors in all mice compared with the PBS control group.

Particularly, the tumor disappeared by day 14, based on the measured tumor volume. There was no weight loss or any other signs of toxicity during the administration period (FIG. 8B). The highly potent in-vivo efficacy of the anti-AML agents, Compound 33 (LDD-2635) and Compound 28 (LDD-2633), by oral administration should be noticeable in terms of generally poor PK profiles of indirubin analogues such as Compound 4 (LDD-1937), of which in-vivo efficacy was similarly achieved with 10 mg/kg dose by intravenous administration only. (FIG. 2)

Although specific parts of the present invention have been described in detail, it will be apparent to those skilled in the art that these specific techniques are merely a preferred embodiment and that the scope of the present invention is not limited thereto. Therefore, the substantial scope of the present invention will be defined by the accompanying claims and their equivalents.

The invention claimed is:

1. A compound represented by Chemical Formula 1 below, a pharmaceutically acceptable salt, a solvate or a hydrate thereof:

[Chemical Formula 1]

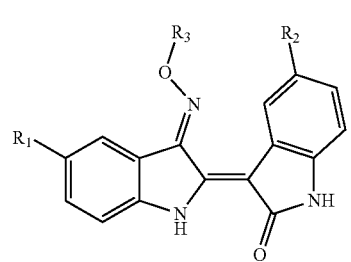

in the Chemical Formula 1, $R_1$ is hydrogen, $R_2$ is fluoro or $C_1$-$C_4$ alkyl ester and $R_3$ is

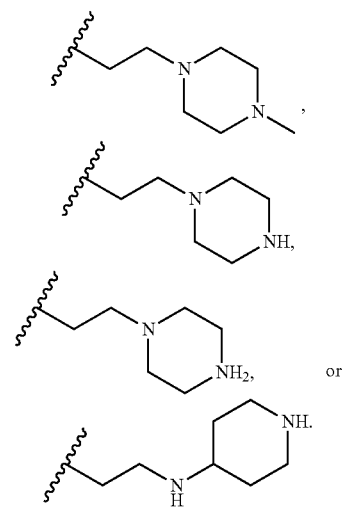

2. The compound, a pharmaceutically acceptable salt, a solvate or a hydrate thereof of claim 1, wherein the $R_3$ is

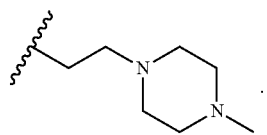 [SMILES: *CCN1CCN(C)CC1]

3. The compound, a pharmaceutically acceptable salt, a solvate or a hydrate thereof of claim 1, wherein the $R_3$ is

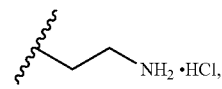

-continued

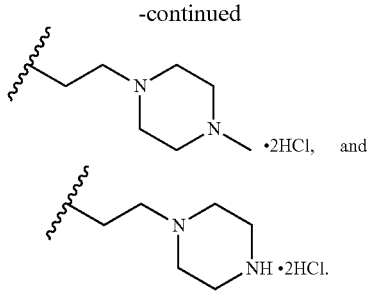

·2HCl, and

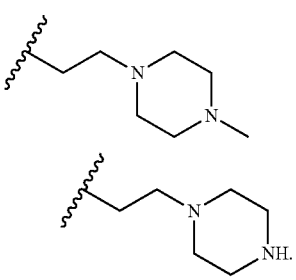
·2HCl.

4. The compound, a pharmaceutically acceptable salt, a solvate or a hydrate thereof of claim 1, wherein the R₃ is

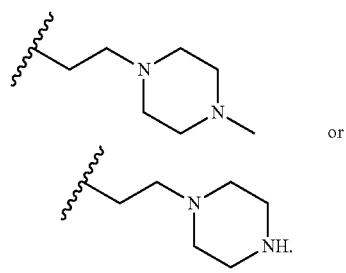
or

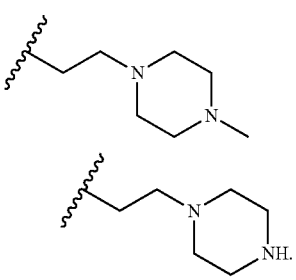
NH.

5. The compound, a pharmaceutically acceptable salt, a solvate or a hydrate thereof of claim 1, wherein the R₂ is $C_1$-$C_4$ alkyl ester.

6. The compound, a pharmaceutically acceptable salt, a solvate or a hydrate thereof of claim 5, wherein the $C_1$-$C_4$ alkyl ester is methyl ester.

7. The compound, a pharmaceutically acceptable salt, a solvate or a hydrate thereof of claim 5, wherein the R₃ is any one of substituents selected from the group consisting of

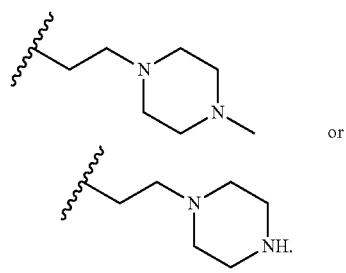
and

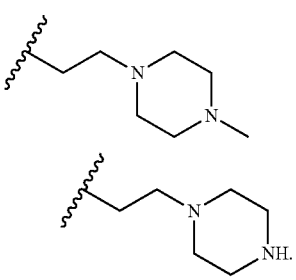

8. The compound, a pharmaceutically acceptable salt, a solvate or a hydrate thereof of claim 1, wherein the compound represented by the Chemical Formula 1 is any one selected from the group consisting of the following compounds:

methyl (2Z,3E)-2'-oxo-3-((2-(piperazin-1-yl)ethoxy)imino)-[2,3'-biindolinylidene]-5'-carboxylate,
methyl (2Z,3E)-3-((2-(4-methylpiperazin-1-yl)ethoxy)imino)-2'-oxo-[2,3'-biindolinylidene]-5'-carboxylate,
(2Z,3E)-5'-fluoro-3-((2-(piperazin-1-yl)ethoxy)imino)-[2,3'-biindolinylidene]-2'-one,
(2Z,3E)-5'-fluoro-3-((2-(4-methylpiperazin-1-yl)ethoxy)imino)-[2,3'-biindolinylidene]-2'-one, and
(2Z,3E)-5'-fluoro-3-((2-(piperidin-4-ylamino)ethoxy)imino)-[2,3'-biindolinylidene]-2'-one.

9. The compound, a pharmaceutically acceptable salt, a solvate or a hydrate thereof of claim 1, wherein the compound represented by the Chemical Formula 1 has an $IC_{50}$ value for FLT3 inhibition of 100 nM or less.

10. The compound, a pharmaceutically acceptable salt, a solvate or a hydrate thereof of claim 1, wherein the compound represented by the Chemical Formula 1 has an $IC_{50}$ value for FLT3 inhibition of 20 nM or less.

11. A pharmaceutical composition comprising: (a) a compound represented by Chemical Formula 1 below, a pharmaceutically acceptable salt, a solvate or a hydrate thereof; and (b) a pharmaceutically acceptable carrier:

[Chemical Formula 1]

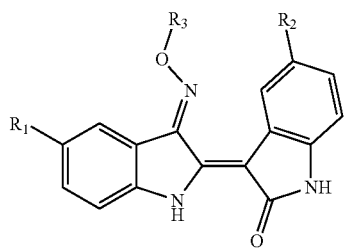

in the Chemical Formula 1, R₁ is hydrogen, R₂ is fluoro or $C_1$-$C_4$ alkyl ester, and R₃ is

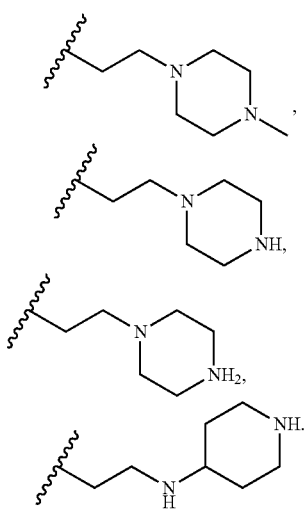

12. The pharmaceutical composition of claim 11, wherein the R₃ is

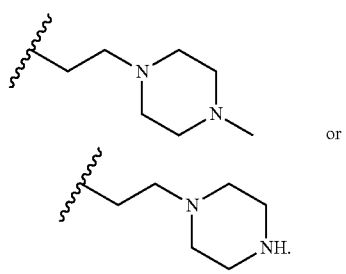

13. The pharmaceutical composition of claim 11, wherein the compound represented by the Chemical Formula 1 is any one selected from the group consisting of the following compounds:

methyl (2Z,3E)-2'-oxo-3-((2-(piperazin-1-yl)ethoxy) imino)-[2,3'-biindolinylidene]-5'-carboxylate, methyl (2Z,3E)-3-((2-(4-methylpiperazin-1-yl)ethoxy) imino)-2'-oxo-[2,3'-biindolinylidene]-'-carboxylate, (2Z,3E)-5'-fluoro-3-((2-(piperazin-1-yl)ethoxy)imino)-[2,3'-biindolinylidene]-2'-one, (2Z,3E)-5'-fluoro-3-((2-(4-methylpiperazin-1-yl)ethoxy) imino)-[2,3'-biindolinylidene]-2'-one, and (2Z,3E)-5'-fluoro-3-((2-(piperidin-4-ylamino)ethoxy) imino)-[2,3'-biindolinylidene]-2'-one.

14. The compound, a pharmaceutically acceptable salt, a solvate or a hydrate thereof of claim 1, wherein the $R_2$ is fluoro.

15. The compound, a pharmaceutically acceptable salt, a solvate or a hydrate thereof of claim 14, wherein the $R_3$ is any one of substituents selected from the group consisting of

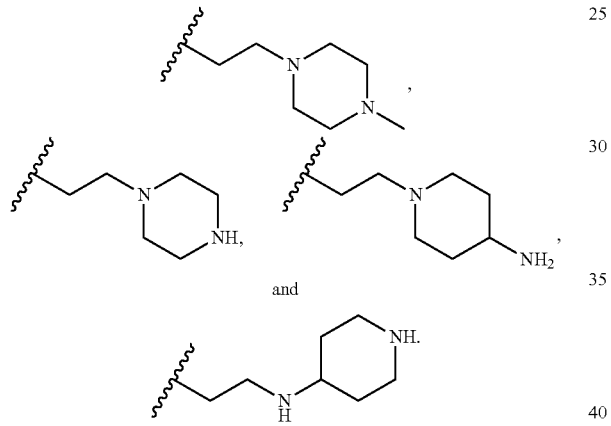

16. The pharmaceutical composition of claim 11, wherein the $R_2$ is fluoro and $R_3$ is any one of substituents selected from the group consisting of

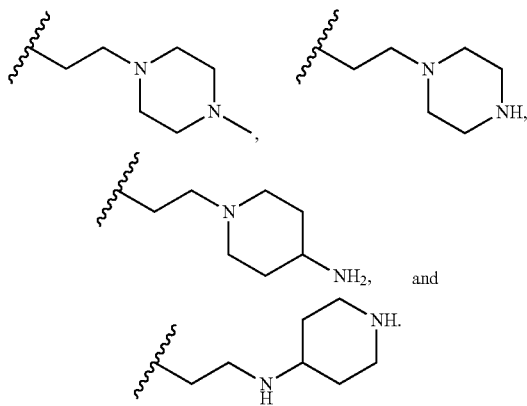

17. The pharmaceutical composition of claim 11, wherein the $R_2$ is $C_1$-$C_4$ alkyl ester.

18. The pharmaceutical composition of claim 17, wherein the $C_1$-$C_4$ alkyl ester is methyl ester and the $R_3$ is any one of substituents selected from the group consisting of

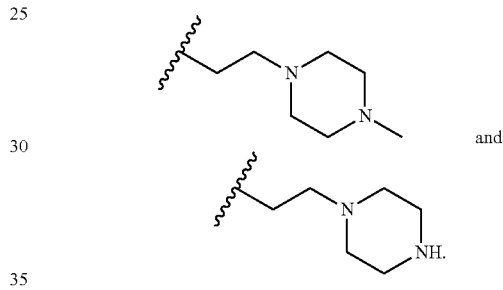

19. A method of treating acute myeloid leukemia or metastatic breast cancer, comprising administering the compound, a pharmaceutically acceptable salt, a solvate or a hydrate thereof of claim 1 to a subject in need thereof.

20. A method of treating acute myeloid leukemia or metastatic breast cancer, comprising administering the pharmaceutical composition of claim 11 to a subject in need thereof.

* * * * *